United States Patent
Xu et al.

(10) Patent No.: US 11,590,109 B2
(45) Date of Patent: Feb. 28, 2023

(54) APPLICATIONS OF NOVEL THIAZOLE DERIVATIVE IN TREATING VIRUS INFECTION

(71) Applicants: EAST CHINA UNIVERSITY OF SCIENCE AND TECHNOLOGY, Shanghai (CN); INSTITUT PASTEUR OF SHANGHAI, CHINESE ACADEMY OF SCIENCES, Shanghai (CN)

(72) Inventors: Ke Xu, Shanghai (CN); Honglin Li, Shanghai (CN); Yufang Xu, Shanghai (CN); Zhenjiang Zhao, Shanghai (CN); Lili Zhu, Shanghai (CN); Wenlin Song, Shanghai (CN); Yi Tong, Shanghai (CN)

( * ) Notice: Subject to any disclaimer, the term of this patent is extended or adjusted under 35 U.S.C. 154(b) by 0 days.

(21) Appl. No.: 16/306,465

(22) PCT Filed: Jun. 2, 2017

(86) PCT No.: PCT/CN2017/087077
§ 371 (c)(1),
(2) Date: Nov. 30, 2018

(87) PCT Pub. No.: WO2017/206955
PCT Pub. Date: Dec. 7, 2017

(65) Prior Publication Data
US 2019/0134008 A1     May 9, 2019

(30) Foreign Application Priority Data
Jun. 3, 2016 (CN) .......................... 201610392348.9

(51) Int. Cl.
*A61K 31/426* (2006.01)
*A61P 31/12* (2006.01)
*C07D 277/50* (2006.01)

(52) U.S. Cl.
CPC ............ *A61K 31/426* (2013.01); *A61P 31/12* (2018.01); *C07D 277/50* (2013.01); *Y02A 50/30* (2018.01)

(58) Field of Classification Search
CPC ..... A61K 31/426; A61P 31/12; Y02A 50/391; Y02A 50/389; Y02A 50/385; C07D 277/50
See application file for complete search history.

(56) References Cited

U.S. PATENT DOCUMENTS 4,319,026 A     3/1982   Hedrich et al.

FOREIGN PATENT DOCUMENTS

| CN | 103006653 A | 4/2013 | |
|----|-------------|--------|---|
| CN | 106892878 A | 6/2017 | |
| DE | 1 040 372 B | 10/1958 | |
| WO | WO-2011150413 A1 * | 12/2011 | ......... A61K 31/4245 |

OTHER PUBLICATIONS

Li et al., Rational Design of Benzylidenehydrazinyl-Substituted Thiazole Derivatives as Potent Inhibitors of Human Dihydroorotate Dehydrogenase with in Vivo Anti-arthritic Activity, Scientific Reports (2015), 5, 14836 (Year: 2015).*

English Translation of the International Search Report corresponding to PCT/CN2017/087077 dated Sep. 11, 2017, 4 pages.

Li, Shiliang et al., "Rational Design of Benzylidenehydrazinyl-Substituted Thiazole Derivatives as Potent Inhibitors of human Dihydroorotate Dehydrogenase with in Vivo Anti-arthritic Activity," *Scientific Reports* (Oct 7, 2015); 5(14836):1-19.

* cited by examiner

*Primary Examiner* — Kortney L. Klinkel
*Assistant Examiner* — Jason Deck
(74) *Attorney, Agent, or Firm* — Mintz Levin Cohn Ferris Glovsky and Popeo, P.C.

(57) ABSTRACT

Provided are applications of a thiazole derivative in treating virus infection and in the preparation of drugs for treating virus infection. Specifically, provided are applications of a compound represented by formula (I) and a pharmaceutical composition comprising the compound represented by formula (I) in treating virus infection and in the preparation of drugs for treating virus infection:

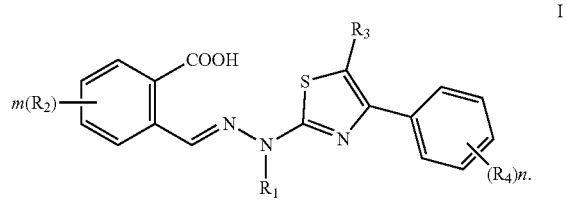

6 Claims, 3 Drawing Sheets

APPLICATIONS OF NOVEL THIAZOLE DERIVATIVE IN TREATING VIRUS INFECTION

TECHNICAL FIELD

The present invention relates to the field of medicinal chemistry. In particular, the present invention relates to the use of novel thiazole derivatives for preparing a medicament for the treatment of viral infections and for treating viral infections.

BACKGROUND

Diseases caused by acute viral infections are important threats to public health and safety. These viruses include not only well-known influenza viruses (avian influenza viruses), hand-foot-and-mouth viruses, dengue viruses, but also include new and sudden severe virus, for example RNA viruses, such as Ebola and coronaviruses. Diseases caused by acute viral infections have some common characteristics: 1) Short course of disease (1-2 weeks), rapid development (rapid development within a few days after onset); 2) It is easy to cause severe illness and even death in high-risk populations; 3) It is easy to spread among people; 4) Rapid replication of the virus usually causes excessive inflammation.

Taking influenza virus as an example, according to statistics from US CDC, the mortality rate of adults hospitalized due to influenza virus infection is 5%-10%, and about 20,000 people die from influenza virus infection every year. This number does not include millions of deaths caused by several famous influenza pandemics, as well as the outbreak caused by avian influenza viruses such as H7N9, H5N1, H5N6 and even H1N1. The course of influenza virus infection is about 14 days, and for critically ill patients, conditions deteriorate rapidly until death within a few days after the onset. Although the critically ill patients were also given specific antiviral drugs such as Tamiflu, the concentration of virus is too high in the late stage of the disease, suppressive effects are limited and lives cannot be saved.

Currently, there are mainly two prescription drugs, Oseltamivir (trade name "Duffy", Roche) and Zanamivir (trade name "Leeqing", GSK) for treating influenza virus infection. These two drugs are inhibitors to the ceramidase of virus and can inhibit the release of the virus, therefore it is clinically proven that the disease time can be shortened and the risk of complications can be reduced. However, due to the action mechanism, if both of the drugs are not used during the early stage of virus infection (48 hours after the onset of symptoms), their effectiveness will be greatly reduced. Recently, Favipiravir, a new anti-influenza virus drug developed by Fukuyama Chemical Co., Ltd., was approved for being marketed. It is aimed at the viral polymerase and can inhibit the replication of the virus. In theory, it will show better antiviral effects, as compared with the above two drugs, and will be more effective when used in the late stage of the disease. According to estimates, the global annual sale of anti-influenza drugs exceeds 200 million US dollars, and the market is mainly located in developed countries such as Europe and the United States. Taking the drug demand in countries with high poultry density in Asia into consideration, the future market for anti-influenza drugs is undoubtedly huge.

At present, antiviral drugs mainly target functional proteins of viruses, that is, specific drugs are needed to be developed for each virus. Such antiviral drug can achieve high specificity and selectivity, however drug-resistance will often occur after a drug is use in long-term and high amount. And if different drugs are developed for different viruses, the development cycle is long and the cost is high.

As a parasitic living organism, a virus must rely on the resources of host cells for reproduction. Therefore, there is an urgent need in the art for small molecule drugs designed for host molecules on which the virus depends, so as to obtain a broad spectrum antiviral drug.

SUMMARY OF THE INVENTION

An object of the present invention is to provide a novel, broad-spectrum compound having antiviral infection activities as a therapeutic agent for viral infections.

In a first aspect, a use of a compound of Formula I, or a pharmaceutically acceptable salt thereof is provided in the present invention for preparing a medicament for the treatment of viral infections:

wherein,

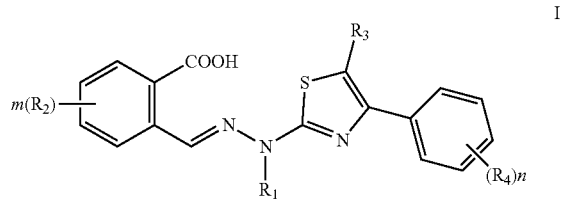

I $R_1$ is selected from the group consisting of H, a substituted or unsubstituted $C_1$-$C_6$ alkyl and C3-C6 cycloalkyl;

$R_2$ is independently selected from the group consisting of H, halogen, a substituted or unsubstituted C1-C6 alkyl, substituted or unsubstituted C1-C6 alkoxy, CN, $NO_2$, hydroxy and $NR^aR^b$;

$R^a$, $R^b$ are independently selected from H or C1-C6 alkyl;

$R_3$ is selected from the group consisting of H and a substituted or unsubstituted C1-C6 alkyl;

$R_4$ is selected from the group consisting of H and halogen;

m is an integer from 0 to 4;

n is an integer from 0 to 5.

In a specific embodiment, the virus is an RNA virus, including but not limited to: influenza virus, respiratory syncytial virus, hand-foot-and-mouth virus (EV71), dengue virus (type 2 dengue virus), Zika virus, Japanese encephalitis virus.

In a preferred embodiment, the influenza virus includes, but is not limited to, H3N2 influenza virus, H1N1 influenza virus, H7N9 influenza virus.

In a specific embodiment the compound is shown in Formula II:

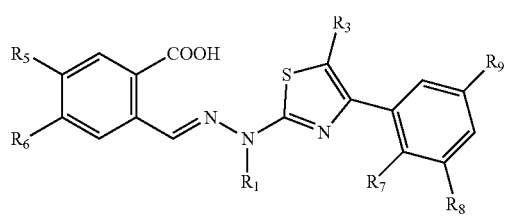

Wherein, $R_5$ and $R_6$ are independently selected from the group consisting of H, halogen, a substituted or unsubstituted C1-C6 alkyl, substituted or unsubstituted C1-C6 alkoxy, hydroxy and $NH_2$;

$R_7$, $R_8$ and $R_9$ are independently selected from the group consisting of H and halogen;

$R_1$ and $R_3$ are described as above.

In a specific embodiment, $R_1$ is selected from the group consisting of H and a C1-C6 alkyl; $R_3$ is selected from the group consisting of H and a substituted or unsubstituted C1-C6 alkyl; $R_5$ and $R_6$ are independently selected from the group consisting of H, halogen, and an unsubstituted or halogen-substituted $C_1$-$C_3$ alkyl; $R_7$ and $R_8$ are independently selected from the group consisting of H and halogen; and $R_9$ is H.

In a specific embodiment, the compound of formula I or a pharmaceutically acceptable salt thereof is selected from the following group:

| No. | Structure |
|---|---|
| 1 | 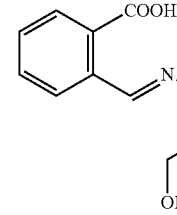 |
| 2 | 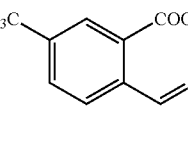 |
| 3 | 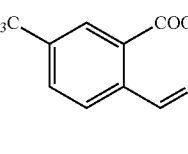 |
| 4 | 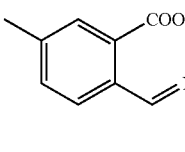 |
| 5 | 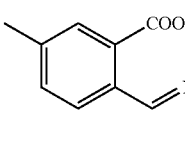 |
| 6 | 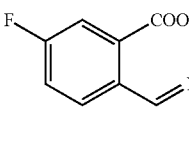 |

-continued

| No. | Structure |
|---|---|
| 7 | 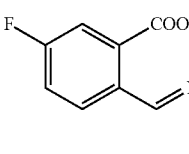 |
| 8 | 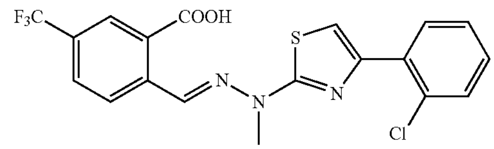 [SMILES: CN(/N=C/c1ccc(C(F)(F)F)cc1C(=O)O)c1nc(-c2ccccc2Cl)cs1] |
| 8-1 | 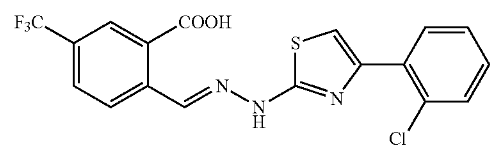 [SMILES: O=C(O)c1cc(C(F)(F)F)ccc1/C=N/Nc1nc(-c2ccccc2Cl)cs1] |
| 9 | 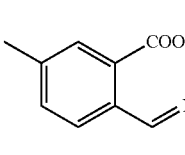 |
| 9-1 | 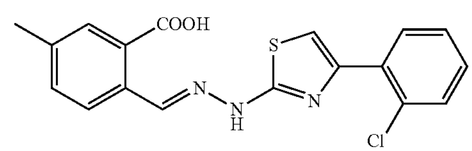 [SMILES: Cc1ccc(/C=N/Nc2nc(-c3ccccc3Cl)cs2)c(C(=O)O)c1] |
| 10 | 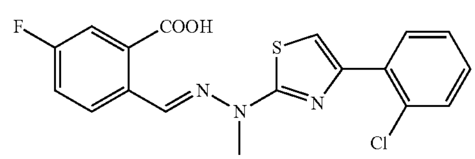 [SMILES: CN(/N=C/c1ccc(F)cc1C(=O)O)c1nc(-c2ccccc2Cl)cs1] |
| 10-1 | 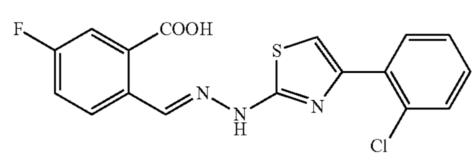 [SMILES: O=C(O)c1cc(F)ccc1/C=N/Nc1nc(-c2ccccc2Cl)cs1] |
| 11 | 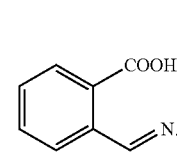 |
| 12 | 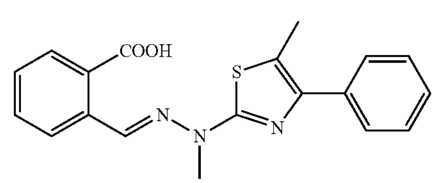 [SMILES: Cc1sc(N(C)/N=C/c2ccccc2C(=O)O)nc1-c1ccccc1] |

| No. | Structure |
|---|---|
| 12-1 | 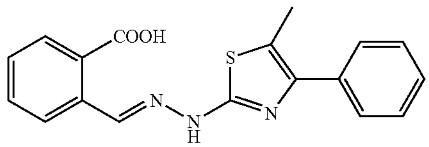 [SMILES: Cc1sc(N/N=C/c2ccccc2C(=O)O)nc1-c1ccccc1] |
| 13 | 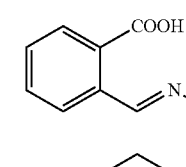 |
| 14 | 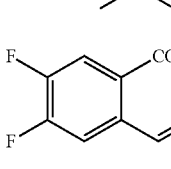 |
| 15 | 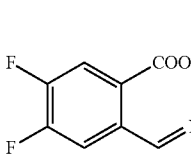 |
| 16 | 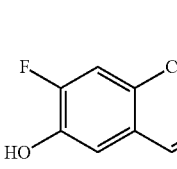 |
| 17 | 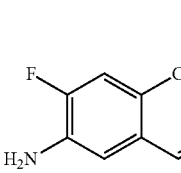 |
| 18 | 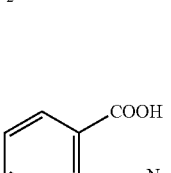 |
| 19 | 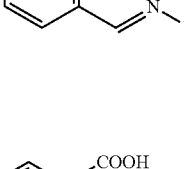 |
| 20 | 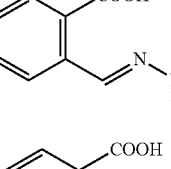 |
| 21 | 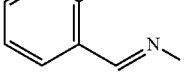 |
| 22 | |
| 23 | |
| 23-1 | |
| 24 | |
| 25 | |
| 52 |  |
| 53 | |
| 54 |  |

| No. | Structure |
|---|---|
| 55 | 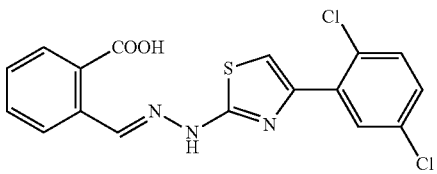 [SMILES: O=C(O)c1ccccc1/C=N/Nc1nc(-c2cc(Cl)ccc2Cl)cs1] |
| 56 | 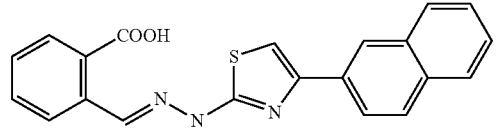 |
| 57 | 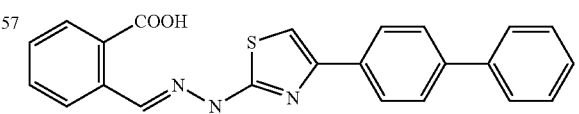 |
| 58 | 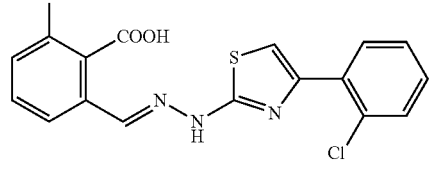 |
| 59 | 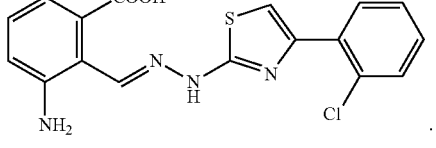 |
In a specific embodiment, the compound is selected from the following group:
| No. | Structure |
|---|---|
| 1 | 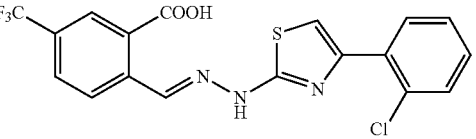 |
| 2 | 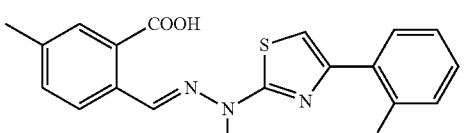 |
| 8 | 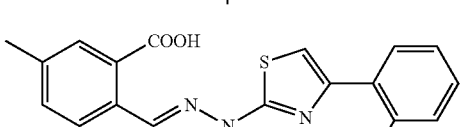 |
| 8-1 | 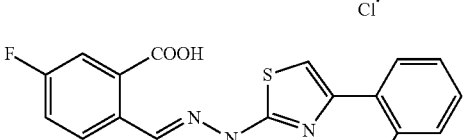 |
| 9 | 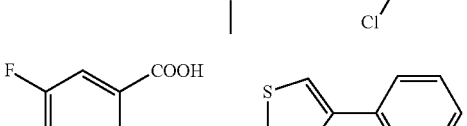 |
| 9-1 | 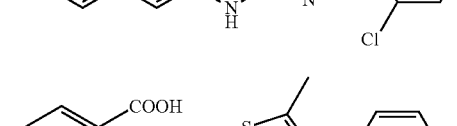 |
| 10 | 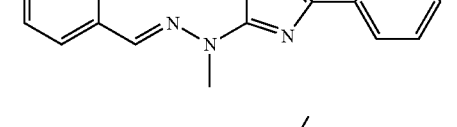 |
| 10-1 | 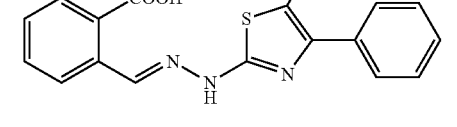 |
| 12 | 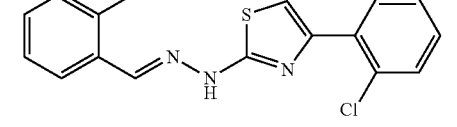 |
| 12-1 | 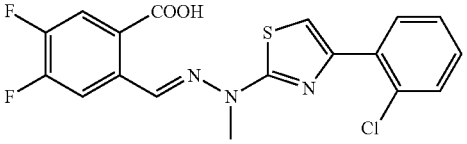 |
| 16 | 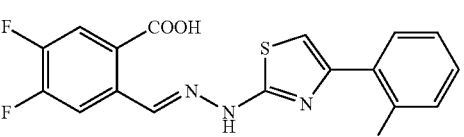 |
| 23 | 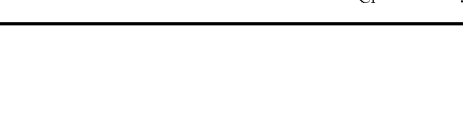 |
| 23-1 | 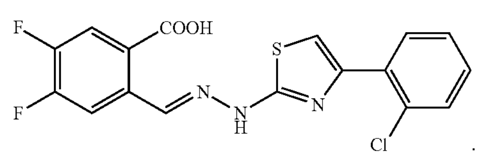 [SMILES: O=C(O)c1cc(F)c(F)cc1/C=N/Nc1nc(-c2ccccc2Cl)cs1] |

In a second aspect, a pharmaceutical composition is provided in the present invention comprising a compound of the first aspect of the invention or a pharmaceutically acceptable salt thereof in combination with other antiviral drugs, and a pharmaceutically acceptable carrier or excipient.

In a preferred embodiment, the pharmaceutical composition comprises Compound 16 or a pharmaceutically acceptable salt thereof in combination with Oseltamivir, and a pharmaceutically acceptable carrier or excipient.

In a third aspect, the use of a pharmaceutical composition comprising a compound according to the first aspect of the invention or a pharmaceutically acceptable salt thereof and a pharmaceutically acceptable carrier or excipient is provided in the present invention for preparing a medicament for the treatment of viral infections.

In a fourth aspect, a pharmaceutical composition is provided in the present invention, wherein the pharmaceutical composition is used for treating viral infections and comprises a compound of the first aspect of the invention or a pharmaceutically acceptable salt thereof, and a pharmaceutically acceptable carrier or excipient.

In a preferred embodiment, the pharmaceutical composition is a dosage form suitable for oral administration, including but not limited to a tablet, solution, suspension, capsule, granule, powder.

In a fifth aspect, a method for treating viral infections is provided in the present invention, comprising administering a compound of the first aspect of the invention or the pharmaceutical composition of the second or fourth aspect of the invention to a subject in need of treatment of viral infections.

In a preferred embodiment, the virus is an RNA virus, including but not limited to influenza virus, respiratory syncytial virus, hand-foot-and-mouth virus (EV71), dengue virus (type 2 dengue virus), Zika virus, Japanese encephalitis virus.

In a further preferred embodiment, the influenza virus includes, but is not limited to, H3N2 influenza virus, H1N1 influenza virus, H7N9 influenza virus.

It is to be understood that, within the scope of the present invention, various technical features of the present invention and the technical features specifically described hereinafter (as in the Examples) may be combined with each other to constitute new or preferred technical solutions, which will not described one by one herein.

MODE FOR CARRYING OUT THE INVENTION

Figure 1:
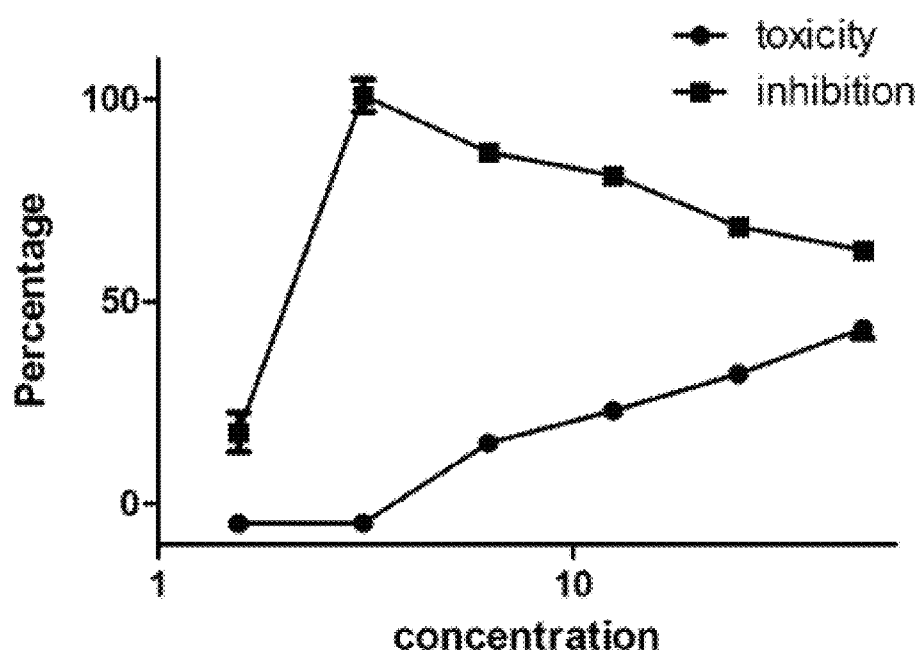
FIG. 1 shows inhibitory effects and cytotoxicity of Compound 16 on influenza virus.

After extensive and intensive research, the inventors unexpectedly discovered a series of thiazole derivatives with broad spectrum and excellent antiviral activities. And these compounds exhibit lower toxicity. The present invention has been completed based the above discoveries.

The present inventors designed novel compounds against nucleic acid synthesis of host cells, and obtained optimal candidate compounds by screening toxicity and function of the compounds. Since viral replication is heavily dependent on the nucleic acid resource of the host cell, excessive inflammatory responses caused by viral infection also depend on gene expression. Therefore, on the one hand, the replication of virus can be inhibited by preventing nucleic acid synthesis of the host cell and the excessive inflammatory responses can be also inhibited on the other hand. In a normal cell, since the gene synthesis and expression are in a certain steady state, and the cell won't excessively depend on the synthesis of new nucleic acids, the compound of the present invention is less toxic to normal cells, and more effective to virus-infected cells.

Definition on Terms

Some groups mentioned herein are defined as follows:

As used herein, "alkyl" refers to a saturated branched or straight-chain alkyl in a carbon chain length of 1 to 10 carbon atoms, and a preferred alkyl includes an alkyl having from 2 to 8 carbon atoms, 1 to 6, 1 to 4 and 1-3 carbon atoms. Examples of alkyl include, but are not limited to, methyl, ethyl, n-propyl, isopropyl, n-butyl, isobutyl, heptyl and the like. The alkyl may be substituted by one or more substituents, for example halogen or haloalkyl. For example, the alkyl may be an alkyl substituted with 1 to 4 fluorine atoms, such as trifluormethyl, or the alkyl may be an alkyl substituted with a fluoroalkyl.

As used herein, "cycloalkyl" means a saturated alkyl with alicyclic structure, for example, a C3-C6 cycloalkyl. In a specific embodiment, the cycloalkyl includes, but is not limited to, cyclopropyl, cyclobutyl, cyclopentyl or cyclohexyl. The cycloalkyl described herein may be substituted or unsubstituted, including but not limited to, substituted with one or more halogen atoms, such as fluorine atoms.

As used herein, "amino" refers to a group of the formula "$NR_xR_y$", wherein $R_x$ and $R_y$ may be independently selected from H or a $C_1$-$C_3$ alkyl or $C_1$-$C_3$ haloalkyl. In a specific embodiment, "amino" as used herein refers to $NH_2$.

As used herein, "halogen" refers to fluoro, chloro, bromo and iodo. In a preferred embodiment, the halogen is chlorine or fluorine; more preferably fluorine.

Compounds of the Invention

The present inventors have unexpectedly discovered a series of thiazole derivatives having broad spectrum and excellent antiviral activities. These compounds show excellent antiviral activities in animal experiments.

In a specific embodiment, the compound of the invention is a compound of formula I or a pharmaceutically acceptable salt thereof:
wherein,

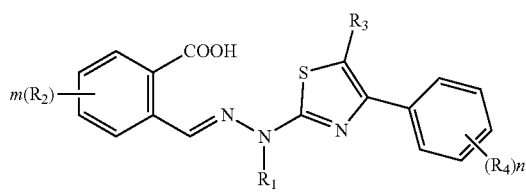

I $R_1$ is selected from the group consisting of H, a substituted or unsubstituted $C_1$-$C_6$ alkyl and C3-C6 cycloalkyl;

$R_2$ is independently selected from the group consisting of H, halogen, a substituted or unsubstituted C1-C6 alkyl, substituted or unsubstituted C1-C6 alkoxy, CN, $NO_2$, hydroxy and $NR^aR^b$;

$R^a$, $R^b$ are independently selected from H or C1-C6 alkyl;

$R_3$ is selected from the group consisting of H and a substituted or unsubstituted C1-C6 alkyl;

$R_4$ is selected from the group consisting of H and halogen;

m is an integer from 0 to 4;

n is an integer from 0 to 5.

In a preferred embodiment, the compound is shown in Formula II:

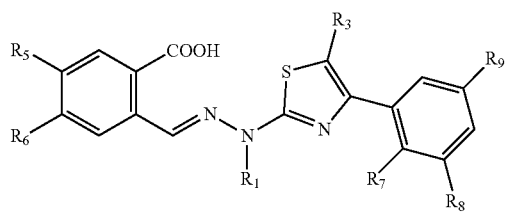

Wherein, $R_5$ and $R_6$ are independently selected from the group consisting of H, halogen, a substituted or unsubstituted C1-C6 alkyl, substituted or unsubstituted C1-C6 alkoxy, hydroxy and $NH_2$;

$R_7$, $R_8$ and $R_9$ are independently selected from the group consisting of H and halogen;

$R_1$ and $R_3$ are described as above.

In a further embodiment, $R_1$ is selected from the group consisting of H and a C1-C6 alkyl, preferably a C1-C3 alkyl; $R_3$ is selected from the group consisting of H and a substituted or unsubstituted C1-C6 alkyl, preferably a C1-C3 alkyl; $R_5$ and $R_6$ are independently selected from the group consisting of H, halogen, preferably F and an unsubstituted or halogen-substituted C1-C3 alkyl; $R_7$ and $R_8$ are independently selected from the group consisting of H and halogen, preferably F; and $R_9$ is H.

Virus

The term "virus" as used herein has the same meaning as commonly understood by a skilled person in the art, and consists of a nucleic acid molecule (DNA or RNA) and protein or consists solely of a nucleic acid molecule (e.g., a prion). The virus is small in size and simple in structure. The virus has no cellular structure and the virus itself cannot replicate since it does not have the basic system necessary to achieve metabolism. However, when it contacts a host cell, its nucleic acid material invades the host cell, and new viruses are replicated according to the instructions of the viral gene by the latter's replication system.

The present inventors have unexpectedly discovered that a series of novel thiazole derivatives have good therapeutic effects on viral infection. In a specific embodiment, the virus described herein refers to an RNA virus. RNA virus is a type of biological virus, and their genetic material consists of ribonucleic acid (RNA). Usually, the nucleic acid is single-stranded (ssRNA) and, sometimes double-stranded (dsRNA).

In a specific embodiment, the RNA virus described herein includes, but not limited to, influenza virus, respiratory syncytial virus, hand-foot-and-mouth virus (EV71), dengue virus (type 2 dengue virus), Zika virus, Japanese encephalitis virus. In a preferred embodiment, the influenza virus includes, but not limited to, H3N2 influenza virus, H1N1 influenza virus, H7N9 influenza virus.

Based on the above compounds, a pharmaceutical composition for treating RNA virus infections is further provided in the present invention, comprising a therapeutically effective amount of a compound of the present invention or a pharmaceutically acceptable salt thereof, and a pharmaceutically acceptable carrier or excipient.

Examples of the pharmaceutically acceptable salt of a compound of the invention include, but are not limited to, inorganic and organic acid salts such as hydrochloride, hydrobromide, sulfate, citrate, lactate, tartrate, maleate, fumarate, mandelate and oxalate; and inorganic and organic base salts formed with bases such as sodium hydroxide, tris(hydroxymethyl)aminomethane (TRIS, tromethamine) and N-methyl glucosamine.

While the needs of each individual vary, one skilled in the art can determine the optimal dosage of each active ingredient in the pharmaceutical compositions of the present invention. In general, the compound of the present invention or a pharmaceutically acceptable salt thereof is orally administered to a mammal every day in an amount of from about 0.0025 to 50 mg/kg body weight. Preferably, however, it is about 0.01 to 10 mg per kilogram of oral administration. For example, a unit oral dose can include from about 0.01 to 50 mg, preferably from about 0.1 to 10 mg, of a compound of the invention. The unit dose may be administered one or more times per day in one or more tablets, each tablet containing from about 0.1 to 50 mg, conveniently from about 0.25 to 10 mg of the compound of the invention or a solvate thereof.

The pharmaceutical composition of the present invention can be formulated into a dosage form suitable for various administration routes, including but not limited to, a dosage form suitable for parenteral, subcutaneous, intravenous, intramuscular, intraperitoneal, transdermal, oral, intrathecal, intracranial, intranasal or topical administration for treating tumors and other diseases. The administered amount is an amount effective to ameliorate or eliminate one or more conditions. For the treatment of a particular disease, an effective amount is a dosage sufficient to ameliorate or, in some way, alleviate symptoms associated with a disease. Such a dosage can be administered in a single dose or can be administered according to an effective therapeutic regimen. The administered amount may cure the disease, but usually is to improve symptoms of the disease. Repeated administrations are generally required to achieve the desired improvement in symptoms. The dosage of the drug will be determined according to the age, health and weight of a patient, the type of concurrent treatment, the frequency of treatment, and the desired therapeutic benefits.

The pharmaceutical preparation of the present invention can be administered to any mammal as long as they can obtain therapeutic effects of the compound of the present invention. The most important among these mammals is humans. The compounds of the invention or pharmaceutical compositions thereof are useful for treating ulcerative colitis.

The pharmaceutical preparations of the invention can be prepared in a known manner. For example, it is manufactured by a conventional mixing, granulating, tableting, dissolving, or freeze-drying process. When manufacturing oral formulations, the mixture can be selectively milled by combining solid auxiliary substances and the active compound. If necessary, after adding an appropriate amount of auxiliary substances, the mixture of granules is processed to obtain a tablet or tablet core.

Suitable auxiliary substances are, in particular, fillers, for example sugars, such as lactose or sucrose, mannitol or sorbitol; cellulose preparations or calcium phosphates, such as tricalcium phosphate or calcium hydrogen phosphate; and binders, such as starch pastes, including corn starch, wheat starch, rice starch, potato starch, gelatin, tragacanth, methyl cellulose, hydroxypropyl methyl cellulose, sodium carboxymethyl cellulose, or polyvinylpyrrolidone. If necessary, a disintegrating agent such as the above-mentioned starch, and carboxymethyl starch, crosslinked polyvinylpyrrolidone, agar, or alginic acid or a salt thereof such as sodium alginate may be added. Auxiliary substances can be, in particular, flow regulators and lubricants, for example, silica, talc, stearates such as calcium magnesium stearate, stearic acid or polyethylene glycol. If desired, the tablet core can be provided with a suitable coating that is resistant to gastric juice. For this purpose, a concentrated sugar solution can be applied. Such solutions may contain gum arabic, talc, polyvinylpyrrolidone, polyethylene glycol and/or titanium dioxide, lacquer solutions and suitable organic solvents or solvent mixtures. For preparing a gastric juice-resistant coating, a suitable cellulose solution such as cellulose acetate ortho-phthalate or hydroxypropyl methylcellulose ortho-phthalate can be used. A dye or pigment can be added to the coating of the tablet or tablet core for, for example, identification or for characterizing the combination of dosages of active ingredients.

In further studies, the inventors have unexpectedly discovered that better therapeutic effects can be produced by the compounds of the invention in combination with other antiviral drugs, such as Oseltamivir. Accordingly, a pharmaceutical composition is further provided in the present invention, comprising a compound of the present invention or a pharmaceutically acceptable salt thereof in combination with other antiviral drug, such as Oseltamivir, and a pharmaceutically acceptable carrier or excipient.

In a preferred embodiment, the compound in the pharmaceutical composition of the invention is Compound 16.

Accordingly, a method for treating RNA virus infection is also provided in the present invention, comprising administering to a subject in need of the treatment a compound of the invention or a pharmaceutical composition comprising a compound of the invention.

Methods for administration include, but are not limited to, various methods of administration well known in the art, which can be determined based on the actual circumstances of a patient. The methods include, but are not limited to, parenteral, subcutaneous, intravenous, intramuscular, intraperitoneal, transdermal, buccal, intrathecal, intracranial, nasal or topical administration.

The invention also encompasses the use of a compound of the invention in the manufacture of a medicament for treating RNA virus infection.

Further, a skilled person will, based on the common knowledge in the art and the contents of the present invention, appreciate that a compound of the present invention can form a salt or an ester due to the contained carboxyl, thereby forming a prodrug.

Advantages of the Invention

1. A series of thiazole derivatives having broad spectrum and excellent antiviral activities is firstly discovered in the present invention;

2. The compounds of the invention are less toxic to normal cells;

3. The compound of the present invention lays a material foundation for researching and developing a new generation of antiviral drugs, and thus has important academic value and practical significance.

Technical solutions of the present invention are further described below in combination with specific examples, but the following examples are not intended to limit the invention, and all methods of application according to the principles and technical means of the present invention shall fall within the scope of the invention. Experimental methods in the following examples which do not specify specific conditions are usually carried out according to conventional conditions or conditions recommended by manufacturers. Percentages and parts are calculated by weight unless otherwise stated.

Example 1

(E)-4-(2-chlorophenyl)-2-[1-methyl-2-(2-carboxy-benzylidene)hydrazino]thiazole 1

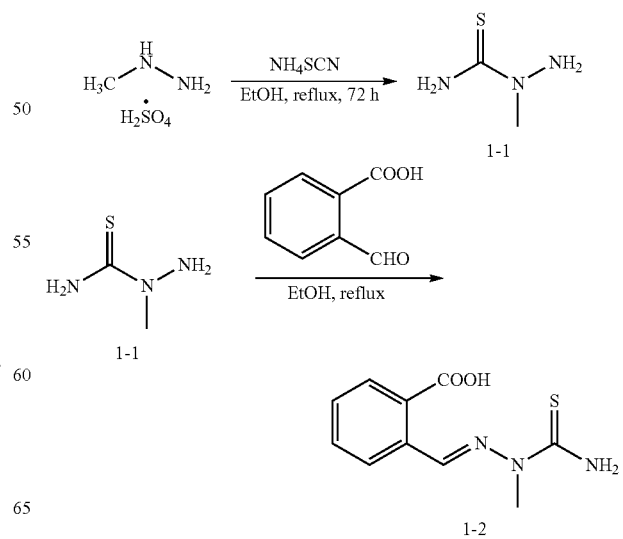

-continued

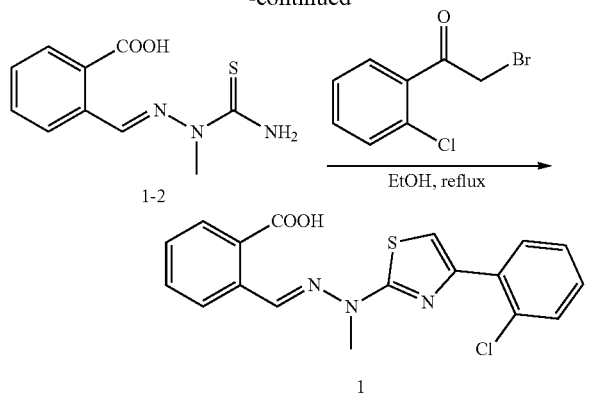

2-methylthiosemicarbazide (1-1)

2.5 g (17.3 mmol) of methyl hydrazine sulfate was weighed into a 250 ml single-mouth flask, 100 ml of ethanol was added, and 1.6 g (20.8 mmol) of ammonium thiocyanate was added with stirring. The reaction mixture was heated to reflux for 72 h. The reaction solution was cooled to room temperature and suction-filtered. The obtained filtrate was then evaporated to dryness and separated through silica gel column chromatography (DCM/MeOH=40:1) to give a second side product as white powdery solids (0.63 g, yield 34.2%).

$^1$H NMR (400 MHz, DMSO-d6, ppm) δ 7.36 (s, 2H), 4.89 (s, 2H), 3.41 (s, 3H). GC-MS (EI) calcd for C2H7N3S [M]+ 105.0, found 105.0.

2-methyl-1-(2-carboxybenzylidene)thiosemicarbazide (1-2)

80 mg (0.76 mmol) of compound (1-1) was weighted into a 50 ml single-mouth flask, 20 ml of ethanol was added, and o-carboxybenzaldehyde (114 mg, 0.76 mmol) was added with stirring. The reaction mixture was heated to reflux, and the reaction was monitored by TLC until the starting materials were completely converted. The reaction solution was cooled to room temperature, and the solvent was evaporated to dryness. The obtained residue was separated through silica gel column chromatography (DCM/MeOH=120:1) to give white powdery solids (100 mg, yield 56%).

$^1$H NMR (400 MHz, DMSO-d$_6$, ppm) δ 13.36 (br, 1H), 8.56 (s, 1H), 8.51 (s, 1H), 8.31 (d, J=7.8 Hz, 1H), 8.25 (s, 1H), 7.88 (d, J=8 Hz, 1H), 7.59 (t, J=7.2 Hz, 1H), 7.50 (t, J=7.2 Hz, 1H), 3.77 (s, 3H). LC-MS (ESI) calcd for C$_{10}$H$_{12}$N$_3$O$_2$S [M+H]$^+$ 238.1, found 238.1.

(E)-4-(2-chlorophenyl)-2-[1-methyl-2-(2-carboxybenzylidene)hydrazino]thiazole 1

100 mg (0.42 mmol) of compound (2) was weighed into a 50 ml single-mouth flask, 10 ml of ethanol was added, and 65 μL (0.42 mmol) of 2'-chloro-2-bromoacetophenone was added with stirring. The reaction mixture was warmed to reflux, and the reaction was monitored by TLC until the starting materials were completely converted. The reaction solution was cooled to room temperature, and the solvent was evaporated to dryness. The obtained residue was separated through silica gel column chromatography (DCM/MeOH=120:1) to give yellow powdery solids (106 mg, yield 67.9%). Mp. 210.4-212.0° C.

$^1$H NMR (400 MHz, DMSO-d6, ppm) δ 13.30 (s, 1H), 8.62 (s, 1H), 8.02 (d, J=7.6 Hz, 1H), 7.98-7.90 (m, 2H), 7.66 (t, J=7.6 Hz, 1H), 7.56-7.49 (m, 2H), 7.47 (s, 1H), 7.43 (td, J$_1$=7.4 Hz, J$_2$=1.2 Hz, 1H), 7.36 (td, J$_1$=7.6 Hz, J$_2$=1.6 Hz, 1H), 3.68 (s, 3H). $^{13}$C NMR (125 MHz, DMSO-d$_6$, ppm) δ 168.98, 168.57, 147.11, 136.94, 135.17, 133.42, 132.48, 131.51, 131.09, 130.98, 130.75, 130.16, 129.45, 129.19, 127.63, 126.51, 111.41, 32.88. HRMS (ESI) calcd for C$_{18}$H$_{15}$N$_3$O$_2$SCl [M+H]$^+$ 372.0574, found 372.0575.

The inventors further synthesized following compounds using a similar method and corresponding starting materials:

(E)-4-(2-chlorophenyl)-2-[1-ethyl-2-(2-carboxybenzylidene)hydrazino]thiazole 2

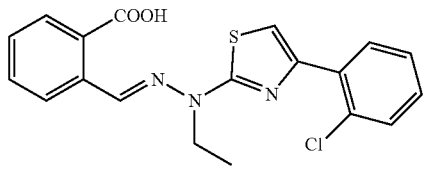 [SMILES: CCN(/N=C/c1ccccc1C(=O)O)c1nc(-c2ccccc2Cl)cs1]

Mp. 203.3-204.1° C. $^1$H NMR (500 MHz, DMSO-d$_6$, ppm) δ 13.32 (br, 1H), 8.64 (s, 1H), 7.98-7.91 (m, 3H), 7.66 (t, J=7.5 Hz, 1H), 7.56-7.46 (m, 2H), 7.45-7.39 (m, 2H), 7.34 (t, J=6.8 Hz, 1H), 4.32 (q, J=6.8 Hz, 2H), 1.27 (t, J=7.0 Hz, 3H). $^{13}$C NMR (125 MHz, DMSO-d$_6$, ppm) δ 168.56, 168.36, 147.34, 137.00, 135.42, 133.53, 132.50, 131.53, 131.12, 130.92, 130.72, 130.22, 129.42, 129.19, 127.62, 126.62, 111.22, 40.38, 10.33. HRMS (ESI) calcd for C$_{19}$H$_{17}$N$_3$O$_2$SCl [M+H]$^+$ 386.0730, found 386.0728.

(E)-4-(2-chlorophenyl)-2-[1-propyl-2-(2-carboxybenzylidene)hydrazino]thiazole 3

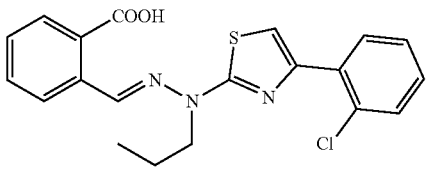 [SMILES: CCCN(/N=C/c1ccccc1C(=O)O)c1nc(-c2ccccc2Cl)cs1]

Mp. 172.6-173.4° C. $^1$H NMR (400 MHz, DMSO-d$_6$, ppm) δ 13.35 (br, 1H), 8.65 (s, 1H), 7.98 (d, J=8.0 Hz, 1H), 7.95-7.92 (m, 2H), 7.67 (t, J=7.2 Hz, 1H), 7.54 (d, J=8.0 Hz, 1H), 7.5 (t, J=7.6 Hz, 1H), 7.45-7.42 (m, 2H), 7.36 (t, J$_1$=7.6 Hz, J$_2$=1.6 Hz, 1H), 4.25 (t, J=7.2 Hz, 2H), 1.82-1.73 (m, 2H), 0.97 (t, J=7.4 Hz, 1H). $^{13}$C NMR (100 MHz, DMSO-d6, ppm) δ 168.54, 168.22, 146.95, 136.63, 134.96, 133.17, 132.11, 131.10, 130.74, 130.55, 130.34, 129.82, 129.04, 128.80, 127.26, 126.09, 110.77, 46.31, 17.98, 11.17. HRMS (ESI) calcd for C20H19N3O2SCl [M+H]$^+$ 400.0887, found 400.0879.

(E)-4-(2-chlorophenyl)-2-[1-isopropyl-2-(2-carboxybenzylidene)hydrazino]thiazole 4

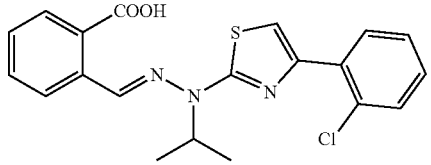 [SMILES: CC(C)N(/N=C/c1ccccc1C(=O)O)c1nc(-c2ccccc2Cl)cs1]

Mp. 185.4-187.0° C. $^1$H NMR (400 MHz, DMSO-d$_6$, ppm) δ 13.35 (br, 1H), 8.91 (s, 1H), 7.99 (d, J=8.0 Hz, 1H), 7.95-7.92 (m, 2H), 7.67 (t, J=7.6 Hz, 1H), 7.54 (d, J=8.0 Hz, 1H), 7.52 (t, J=7.6 Hz, 1H), 7.46-7.42 (m, 2H), 7.36 (td, J$_1$=7.6 Hz, J$_2$=1.6 Hz, 1H), 5.22-5.11 (m, 1H), 1.57 (d, J=6.8 Hz, 6H). $^{13}$C NMR (100 MHz, DMSO-d$_6$, ppm) δ 168.22, 168.21, 146.90, 137.32, 135.23, 133.14, 132.07, 131.06, 130.64, 130.58, 130.39, 129.88, 128.97, 128.78, 127.28, 125.91, 111.12, 49.61, 18.07, 18.07. HRMS (ESI) calcd for C$_{20}$H$_{19}$N$_3$O$_2$SCl [M+H]$^+$ 400.0887, found 400.0885.

(E)-4-(2-chlorophenyl)-2-[1-(2-butyl)-2-(2-carboxybenzylidene)hydrazino]thiazole 5

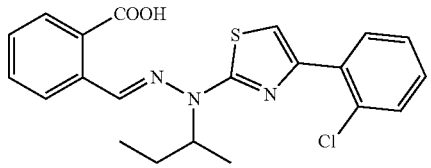 [SMILES: CCC(C)N(/N=C/c1ccccc1C(=O)O)c1nc(-c2ccccc2Cl)cs1]

Mp. 170.5-170.6° C. $^1$H NMR (400 MHz, DMSO-d$_6$, ppm) δ 13.32 (br, 1H), 8.91 (s, 1H), 7.99 (d, J=8.0 Hz, 1H), 7.95-7.90 (m, 2H), 7.67 (t, J$_1$=7.6 Hz, 1H), 7.55-7.48 (m, 2H), 7.46-7.42 (m, 2H), 7.36 (td, J$_1$=7.6 Hz, J$_2$=1.6 Hz, 1H), 5.00-4.93 (m, 1H), 2.35-2.24 (m, 1H), 1.92-1.81 (m, 1H), 1.54 (d, J=6.8 Hz, 3H), 0.88 (t, J=7.2 Hz, 3H). $^{13}$C NMR (100 MHz, DMSO-d$_6$, ppm) δ 168.66, 168.19, 146.97, 137.03, 135.24, 133.19, 132.13, 131.04, 130.67, 130.58, 130.39, 129.70, 128.98, 128.77, 127.29, 125.91, 111.04, 55.67, 25.26, 16.33, 11.14. HRMS (EST) calcd for C$_{21}$H$_{21}$N$_3$O$_2$SCl [M+H]$^+$ 414.1043, found 414.1029.

(E)-4-(2-chlorophenyl)-2-[1-(2-amyl)-2-(2-carboxybenzylidene)hydrazino]thiazole 6

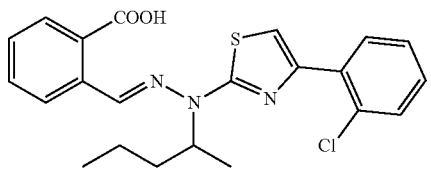 [SMILES: CCCC(C)N(/N=C/c1ccccc1C(=O)O)c1nc(-c2ccccc2Cl)cs1]

Mp. 146.7-147.0° C. $^1$H NMR (400 MHz, DMSO-d$_6$, ppm) δ 13.35 (br, 1H), 8.91 (s, 1H), 7.98 (d, J=7.6 Hz, 1H), 7.94 (d, J=8.0 Hz, 1H), 7.91 (dd, J$_1$=7.6 Hz, J$_2$=1.6 Hz, 1H), 7.67 (t, J=7.6 Hz, 1H), 7.53 (d, J=8.0 Hz, 1H), 7.49 (t, J=7.6 Hz, 1H), 7.46-7.42 (m, 2H), 7.36 (td, J$_1$=7.6 Hz, J$_2$=1.6 Hz, 1H), 5.14-5.06 (m, 1H), 2.34-2.25 (m, 1H), 1.82-1.73 (m, 1H), 1.53 (d, J=6.8 Hz, 3H), 1.34-1.24 (m, 2H), 0.89 (t, J=7.4 Hz, 1H). $^{13}$C NMR (100 MHz, DMSO-d$_6$, ppm) δ 168.68, 168.20, 146.98, 137.04, 135.30, 133.20, 132.14, 131.00, 130.68, 130.59, 130.40, 129.68, 128.99, 127.30, 125.90, 111.09, 53.81, 34.20, 19.46, 16.46, 13.60. HRMS (ESI) calcd for C$_{22}$H$_{23}$N$_3$O$_2$SCl [M+H]$^+$ 428.1200, found 428.1193.

(E)-4-(2-chlorophenyl)-2-[1-hydroxyethyl-2-(2-carboxybenzylidene)hydrazino]thiazole 7

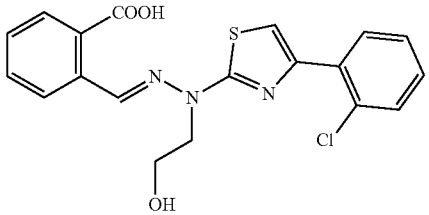 [SMILES: O=C(O)c1ccccc1/C=N/N(CCO)c1nc(-c2ccccc2Cl)cs1]

Mp. 187.9-188.9° C. $^1$H NMR (400 MHz, DMSO-d$_6$, ppm) δ 13.24 (br, 1H), 8.75 (s, 1H), 7.98-7.01 (m, 3H), 7.66 (t, J=7.6 Hz, 1H), 7.54 (d, J=8.0 Hz, 1H), 7.49 (t, J=7.6 Hz, 1H), 7.45-7.41 (m, 2H), 7.36 (td, J$_1$=7.6 Hz, J$_2$=1.6 Hz, 1H), 4.35 (t, J=6.4 Hz, 2H), 3.76 (t, J=6.4 Hz, 2H). $^{13}$C NMR (100 MHz, DMSO-d$_6$, ppm) δ 168.64, 168.23, 146.87, 136.89, 134.91, 133.15, 131.99, 131.19, 130.71, 130.46, 130.32, 130.16, 129.04, 128.79, 127.22, 126.28, 110.78, 56.24, 47.46. HRMS (ESI) calcd for C$_{19}$H$_{17}$N$_3$O$_3$SCl [M+H]$^+$ 402.0679, found 402.0678.

(E)-4-(2-chlorophenyl)-2-[1-methyl-2-(4-trifluoromethyl-2-carboxybenzylidene)hydrazino]thiazole 8

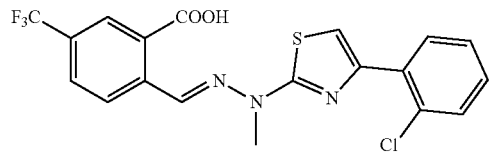 [SMILES: CN(/N=C/c1ccc(C(F)(F)F)cc1C(=O)O)c1nc(-c2ccccc2Cl)cs1]

Mp. 209.3-210.7° C. $^1$H NMR (400 MHz, DMSO-d$_6$, ppm) δ 14.02 (br, 1H), 8.66 (s, 1H), 8.21 (d, J=8.0 Hz, 1H), 8.17 (s, 1H), 8.02 (d, J=8.0 Hz, 1H), 7.95 (d, J=7.6 Hz, 1H), 7.56-7.53 (m, 2H), 7.43 (t, J=7.6 Hz, 1H), 7.37 (t, J=7.6 Hz, 1H), 3.70 (s, 3H). $^{13}$C NMR (100 MHz, DMSO-d$_6$, ppm) δ 168.33, 167.17, 146.79, 138.38, 135.01, 132.91, 131.12, 130.70, 130.37, 129.14, 128.57, 128.25, 128.20, 127.26, 127.04, 125.10, 122.40, 111.51, 32.68. HRMS (ESI) calcd for C$_{19}$H$_{14}$N$_3$O$_2$SClF$_3$ [M+H]$^+$ 440.0447, found 440.0433.

(E)-4-(2-chlorophenyl)-2-[1-methyl-2-(4-methyl-2-carboxybenzylidene)hydrazino]thiazole 9

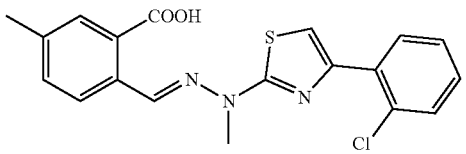 [SMILES: Cc1ccc(/C=N/N(C)c2nc(-c3ccccc3Cl)cs2)c(C(=O)O)c1]

Mp. 231.3-232.5° C. $^1$H NMR (400 MHz, DMSO-d$_6$, ppm) δ 13.30 (br, 1H), 8.59 (s, 1H), 7.96 (d, J=7.6 Hz, 1H), 7.92 (d, J=8.0 Hz, 1H), 7.75 (s, 1H), 7.54 (d, J=7.6 Hz, 1H), 7.49-7.46 (m, 2H), 7.43 (t, J=7.6 Hz, 1H), 7.36 (t, J=7.6 Hz, 1H), 3.66 (s, 3H), 2.38 (s, 3H). $^{13}$C NMR (100 MHz, DMSO-d$_6$, ppm) δ 168.60, 168.35, 146.68, 138.54, 136.64, 133.03, 132.70, 132.07, 131.11, 130.86, 130.67, 130.34, 129.83, 129.00, 127.21, 126.04, 110.84, 32.39, 20.69. HRMS (ESI) calcd for C$_{19}$H$_{17}$N$_3$O$_2$SCl [M+H]$^+$ 386.0730, found 386.0738.

(E)-4-(2-chlorophenyl)-2-[1-methyl-2-(2-carboxyl-4-fluorobenzylidene)hydrazino]thiazole 10

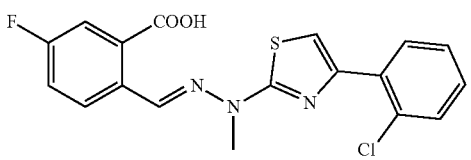 [SMILES: CN(/N=C/c1ccc(F)cc1C(=O)O)c1nc(-c2ccccc2Cl)cs1]

Mp. 228.6-229.7° C. $^1$H NMR (400 MHz, DMSO-d$_6$, ppm) δ 13.28 (br, 1H), 8.14 (s, 1H), 7.93 (dd, J$_1$=7.6 Hz, J$_2$=1.6 Hz, 1H), 7.61 (dd, J$_1$=7.0 Hz, J$_2$=1.8 Hz, 1H), 7.55-7.49 (m, 3H), 7.44-7.41 (m, 1H), 7.36 (td, J$_1$=7.6 Hz, J$_2$=1.6 Hz, 1H), 3.68 (s, 3H). $^{13}$C NMR (100 MHz, DMSO-d$_6$, ppm) δ 168.55, 168.01, 159.74 (d, $^1$J=249 Hz), 146.67, 133.68, 133.10, 131.50, 131.12, 130.72, 130.32, 130.10 (d, $^3$J=8.8 Hz), 129.06, 127.23, 125.53 (d, $^4$J=3.1 Hz), 121.75 (d, $^2$J=11.8 Hz), 118.76 (d, $^2$J=22 Hz), 111.13, 32.28. HRMS (ESI) calcd for C$_{18}$H$_{14}$N$_3$O$_2$FSCl [M+H]$^+$ 390.0479, found 390.0475.

(E)-5-methyl-4-phenyl-2-[1-methyl-2-(4-methyl-2-carboxybenzylidene)hydrazino]thiazole 11

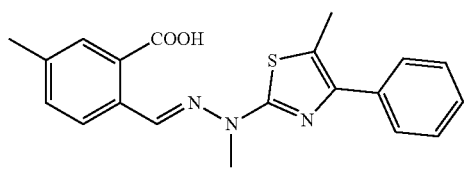 [SMILES: Cc1ccc(/C=N/N(C)c2nc(-c3ccccc3)c(C)s2)c(C(=O)O)c1]

Mp. 243.2-245.2° C. $^1$H NMR (400 MHz, DMSO-d6, ppm) δ 13.24 (br, 1H), 8.54 (s, 1H), 7.91 (d, J=8.0 Hz, 1H), 7.73 (s, 1H), 7.64-7.53 (m, 2H), 7.46-7.42 (m, 3H), 7.33 (t, J=7.4 Hz, 1H), 3.60 (s, 3H), 2.44 (s, 3H), 2.38 (s, 3H). $^{13}$C NMR (100 MHz, DMSO-d$_6$, ppm) δ 168.35, 165.40, 145.43, 138.33, 135.76, 135.16, 132.68, 132.22, 130.86, 129.62, 128.24, 128.24, 127.85, 127.85, 127.06, 125.89, 119.27, 31.85, 20.68, 12.24. HRMS (ESI) calcd for C$_{20}$H$_{20}$N$_3$O$_2$S [M+H]$^+$ 366.1276, found 366.1273.

(E)-5-methyl-4-phenyl-2-[1-methyl-2-(2-carboxybenzylidene)hydrazino]thiazole 12

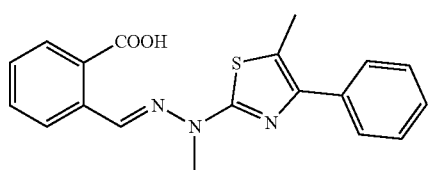 [SMILES: Cc1sc(N(C)/N=C/c2ccccc2C(=O)O)nc1-c1ccccc1]

Mp. 222.7-224.9° C. $^1$H NMR (400 MHz, DMSO-d$_6$, ppm) δ 13.32 (br, 1H), 8.58 (s, 1H), 8.01 (d, J=8.0 Hz, 1H), 7.92 (d, J=7.6 Hz, 1H), 7.68-7.63 (m, 3H), 7.50-7.43 (m, 3H), 7.34 (t, J=7.4 Hz, 1H), 3.62 (s, 3H), 2.44 (s, 3H). $^{13}$C NMR (100 MHz, DMSO-d$_6$, ppm) δ 168.24, 165.36, 145.47, 135.66, 135.13, 134.90, 131.98, 130.58, 129.70, 128.59, 128.25, 128.25, 127.86, 127.86, 127.09, 125.94, 119.44, 31.93, 12.24. HRMS (ESI) calcd for C$_{19}$H$_{16}$N$_3$O$_2$S [M−H]$^−$ 350.0963, found 350.0951.

(E)-4-(2-chlorophenyl)-2-[1-methyl-2-(2-carboxybenzylidene)hydrazino]thiazole 13

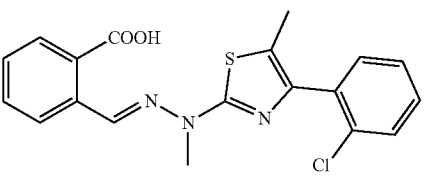 [SMILES: Cc1sc(N(C)/N=C/c2ccccc2C(=O)O)nc1-c1ccccc1Cl]

Mp. 208.8-209.8° C. $^1$H NMR (400 MHz, DMSO-d$_6$, ppm) δ 13.46 (br, 1H), 8.60 (s, 1H), 8.01 (d, J=8.0 Hz, 1H), 7.92 (d, J=8.0 Hz, 1H), 7.64 (t, J=7.4 Hz, 1H), 7.56 (d, J=7.6 Hz, 1H), 7.49-7.39 (m, 4H), 3.56 (s, 3H), 2.15 (s, 3H). $^{13}$C NMR (100 MHz, DMSO-d$_6$, ppm) δ 168.98, 166.46, 144.56, 136.46, 135.29, 134.54, 133.25, 132.50, 132.31, 131.05, 130.72, 130.26, 130.01, 129.09, 127.49, 126.42, 121.85, 32.46, 12.16. HRMS (ESI) calcd for C$_{19}$H$_{17}$N$_3$O$_2$SCl [M+H]$^+$ 386.0730, found 386.0727.

(E)-5-ethyl-4-(2-chlorophenyl)-2-(2-carboxylbenzylidenehydrazino)thiazole 14

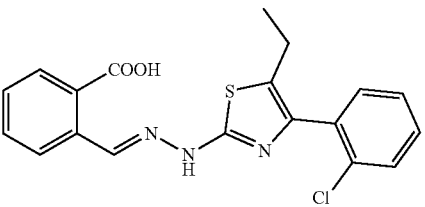 [SMILES: CCc1sc(N/N=C/c2ccccc2C(=O)O)nc1-c1ccccc1Cl]

Mp. 223.9-223.9° C. $^1$H NMR (500 MHz, DMSO-d$_6$, ppm) δ 12.57 (br, 2H), 8.79 (s, 1H), 8.01 (d, J=8.0 Hz, 1H), 7.88 (d, J=8.0 Hz, 1H), 7.62 (t, J=7.5 Hz, 1H), 7.56-7.51 (m, 1H), 7.46 (t, J=7.5 Hz, 1H), 7.44-7.36 (m, 3H), 2.49 (q, J=7.5 Hz, 1H), 1.13 (t, J=7.5 Hz, 3H). $^{13}$C NMR (125 MHz, DMSO-d$_6$, ppm) δ 169.28, 165.92, 144.14, 140.84, 135.89, 135.46, 133.99, 133.03, 133.02, 131.46, 130.81, 130.73, 130.60, 129.73, 128.09, 127.73, 127.01, 20.99, 17.25. HRMS (ESI) calcd for C$_{19}$H$_{17}$N$_3$O$_2$SCl [M+H]$^+$ 386.0730, found 386.0729.

(E)-5-methyl-4-(2-chlorophenyl)-2-(2-carboxylbenzylidenehydrazino)thiazole 15

Mp. 217.6-217.8° C. $^1$H NMR (400 MHz, DMSO-d$_6$, ppm) δ 12.7 (br, 2H), 8.77 (s, 1H), 7.99 (d, J=7.6 Hz, 1H), 7.87 (d, J=7.2 Hz, 1H), 7.62 (t, J=7.4 Hz, 1H), 7.562-7.543 (m, 1H), 7.481-7.397 (m, 4H), 2.14 (s, 3H). $^{13}$C NMR (125 MHz, DMSO-d$_6$, ppm) δ 168.65, 165.18, 144.49, 140.16, 135.25, 134.56, 133.21, 132.46, 130.83, 130.14, 130.03, 129.11, 127.45, 126.37, 119.49, 12.15. HRMS (ESI) calcd for C$_{18}$H$_{15}$N$_3$O$_2$SCl [M+H]+ 372.0574, found 372.0569.

(E)-4-(2-chlorophenyl)-2-(2-carboxybenzylidenehydrazino)thiazole 16

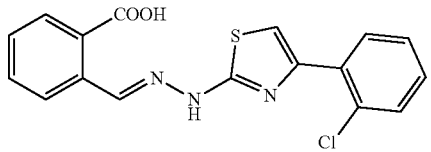 [SMILES: O=C(O)c1ccccc1/C=N/Nc1nc(-c2ccccc2Cl)cs1]

Mp. 200.2-200.9° C. $^1$H NMR (400 MHz, DMSO-d6, ppm) δ 13.2 (br, 1H), 12.4 (br, 1H), 8.82 (s, 1H), 8.00 (d, J=7.6 Hz, 1H), 7.89-7.86 (m, 2H), 7.64 (t, J=7.4 Hz, 1H), 7.53 (dd, J1=7.6 Hz, J2=1.2 Hz, 1H), 7.49 (td, J1=7.6 Hz, J2=1.2 Hz, 1H), 7.42 (td, J1=7.6 Hz, J2=1.2 Hz, 1H), 7.36 (m, 2H). 13C NMR (100 MHz, DMSO-d6, ppm) δ 168.63, 167.77, 147.63, 140.76, 135.08, 133.71, 132.43, 131.54, 131.23, 130.83, 130.83, 130.26, 129.47, 129.28, 127.69, 126.47, 109.26. HRMS (ESI) calcd for C17H13N3O2SCl [M+H]+ 358.0417, found 358.0417.

(E)-5-methyl-4-phenyl-2-(2-carboxylbenzylidenehydrazino)thiazole 17

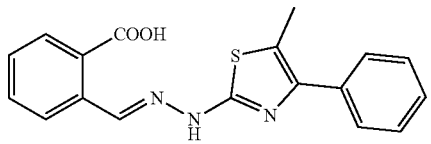 [SMILES: Cc1sc(N/N=C/c2ccccc2C(=O)O)nc1-c1ccccc1]

Mp. 215.9-216.0° C. $^1$H NMR (400 MHz, DMSO-d$_6$, ppm) δ 12.7 (br, 2H), 8.77 (s, 1H), 7.99 (d, J=7.6 Hz, 1H), 7.87 (dd, J$_1$=8.0 Hz, J$_2$=1.2 Hz, 1H), 7.63-7.59 (m, 3H), 7.48-7.43 (m, 3H), 7.33 (t, J=7.2 Hz, 1H), 2.43 (s, 3H). $^{13}$C NMR (125 MHz, DMSO-d$_6$, ppm) δ 168.66, 164.72, 146.00, 140.05, 135.64, 135.24, 132.36, 130.83, 130.12, 129.08, 128.73, 128.73, 128.35, 128.35, 127.51, 126.33, 117.61, 12.74. HRMS (ESI) calcd for C$_{18}$H$_{16}$N$_3$O$_2$S [M+H]$^+$ 338.0963, found 338.0954.

(E)-4-phenyl-2-(2-carboxybenzylidenehydrazino)thiazole 18

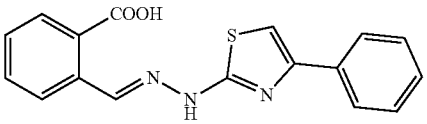 [SMILES: O=C(O)c1ccccc1/C=N/Nc1nc(-c2ccccc2)cs1]

Mp. 163.8-165.6° C. $^1$H NMR (400 MHz, DMSO-d$_6$, ppm) δ 13.45 (br, 1H), 12.49 (br, 1H), 8.81 (s, 1H), 7.99 (d, J=7.6 Hz, 1H), 7.87 (m, 3H), 7.63 (t, J=7.4 Hz, 1H), 7.47 (t, J=7.2 Hz, 1H), 7.41 (t, J=7.6 Hz, 2H), 7.33 (s, 1H), 7.30 (t, J=7.4 Hz, 1H). $^{13}$C NMR (100 MHz, DMSO-d$_6$, ppm) δ 168.53, 168.53, 150.97, 140.58, 135.02, 134.99, 132.31, 130.74, 130.15, 129.15, 128.96, 128.96, 127.90, 126.34, 125.90, 125.90, 104.20. HRMS (ESI) calcd for C$_{18}$H$_{16}$N$_3$O$_2$S [M−H]$^-$ 322.0650, found 322.0656.

(E)-4-(2,5-dichlorophenyl)-2-[1-methyl-2-(2-carboxybenzylidene)hydrazino]thiazole 19

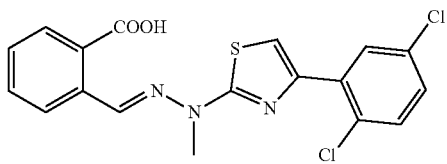 [SMILES: CN(/N=C/c1ccccc1C(=O)O)c1nc(-c2cc(Cl)ccc2Cl)cs1]

Mp. 268.4-269.5° C. $^1$H NMR (400 MHz, DMSO-d$_6$, ppm) δ 13.31 (br, 1H), 8.63 (s, 1H), 8.02-8.00 (m, 2H), 7.93 (d, J=7.2 Hz, 1H), 7.67 (t, J=7.6 Hz, 1H), 7.63 (s, 1H), 7.58 (d, J=7.6 Hz, 1H), 7.50 (t, J=7.2 Hz, 1H), 7.43 (dd, J, =7.2 Hz, J$_2$=2.8 Hz, 1H), 3.68 (s, 3H). $^{13}$C NMR (100 MHz, DMSO-d$_6$, ppm) δ 168.68, 168.15, 145.13, 136.79, 134.70, 134.21, 132.14, 132.06, 131.85, 130.59, 130.17, 129.76, 129.20, 128.84, 128.58, 126.13, 112.31, 32.49. HRMS (ESI) calcd for C$_{18}$H$_{14}$N$_3$O$_2$SCl$_2$ [M+H]$^+$ 406.0184, found 406.0187.

(E)-4-phenyl-2-[1-methyl-2-(2-carboxybenzylidene)hydrazino]thiazole 20

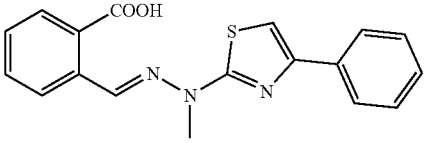 [SMILES: CN(/N=C/c1ccccc1C(=O)O)c1nc(-c2ccccc2)cs1]

Mp. 205.6-206.8° C. $^1$H NMR (400 MHz, DMSO-d$_6$, ppm) δ 13.31 (br, 1H), 8.62 (s, 1H), 8.02 (d, J=7.6 Hz, 1H), 7.94-7.91 (m, 3H), 7.66 (t, J=7.2 Hz, 1H), 7.49 (t, J=7.2 Hz, 1H), 7.45-7.40 (m, 3H), 7.31 (t, J=7.2 Hz, 1H), 3.71 (s, 3H). $^{13}$C NMR (100 MHz, DMSO-d$_6$, ppm) δ 169.45, 168.20, 150.18, 136.35, 134.80, 134.49, 132.07, 130.60, 129.71, 128.76, 128.56, 128.56, 127.59, 126.09, 125.54, 125.54, 105.97, 32.51. HRMS (ESI) calcd for C$_{18}$H$_{16}$N$_3$O$_2$S [M+H]$^+$ 338.0963, found 338.0963.

(E)-4-(3-chlorophenyl)-2-[1-methyl-2-(2-carboxybenzylidene)hydrazino]thiazole 21

Mp. 244.7-245.4° C. $^1$H NMR (400 MHz, DMSO-d$_6$, ppm) δ 13.32 (br, 1H), 8.63 (s, 1H), 8.01 (d, J=7.6 Hz, 1H), 7.97 (s, 1H), 7.93 (d, J=7.6 Hz, 1H), 7.88 (d, J=8.0 Hz, 1H), 7.66 (t, J=7.6 Hz, 1H), 7.61 (s, 1H), 7.50 (t, J=7.6 Hz, 1H), 7.45 (t, J=7.6 Hz, 1H), 7.37 (d, J=8.0 Hz, 1H), 3.71 (s, 3H). $^{13}$C NMR (100 MHz, DMSO-d$_6$, ppm) δ 169.57, 168.18, 148.56, 136.64, 136.50, 134.72, 133.48, 132.06, 130.59, 130.44, 129.76, 128.81, 127.28, 126.12, 125.16, 124.05, 107.56, 32.52. HRMS (ESI) calcd for C$_{18}$H$_{15}$N$_3$O$_2$SCl [M+H]$^+$ 372.0574, found 372.0574.

(E)-5-methyl-4-(2-chlorophenyl)-2-[1-(2-amyl)-2-(2-carboxybenzylidene)hydrazino]thiazole 22

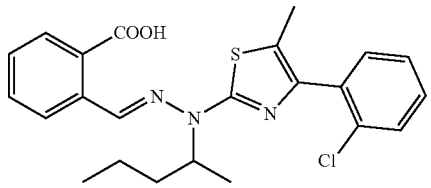 [SMILES: CCCC(C)N(/N=C/c1ccccc1C(=O)O)c1nc(-c2ccccc2Cl)c(C)s1]

Mp. 89.9-90.1° C. $^1$H NMR (400 MHz, DMSO-d$_6$, ppm) δ 13.29 (br, 1H), 8.85 (s, 1H), 7.98 (d, J=8.0 Hz, 1H), 7.92 (d, J=7.6 Hz, 1H), 7.65 (t, J=7.6 Hz, 1H), 7.56-7.54 (m, 1H), 7.51-7.41 (m, 4H), 5.05-4.96 (m, 1H), 2.29-2.22 (m, 1H), 2.16 (s, 3H), 1.75-1.67 (m, 1H), 1.46 (d, J=7.2 Hz, 3H), 1.28-1.23 (m, 2H), 0.87 (t, J=7.6 Hz, 3H). $^{13}$C NMR (100 MHz, DMSO-d$_6$, ppm) δ 168.23, 166.06, 144.08, 136.14, 135.46, 134.09, 132.79, 132.09, 131.93, 130.58, 129.64, 129.60, 129.48, 128.56, 126.95, 125.73, 121.62, 53.39, 34.01, 19.41, 16.35, 13.58, 11.52. HRMS (ESI) calcd for C$_{23}$H$_{25}$N$_3$O$_2$SCl [M+H]$^+$ 442.1356, found 442.1354.

(E)-2-((2-(4-(3-methoxyphenyl)thiazol-2-yl)hydrazono)methyl)benzoic Acid (52)

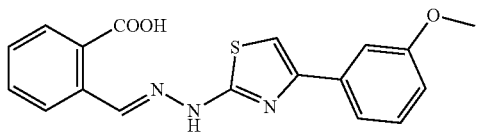 [SMILES: COc1cccc(-c2csc(N/N=C/c3ccccc3C(=O)O)n2)c1]

Mp: 167.3-167.9° C. $^1$H NMR (400 MHz, DMSO-d$_6$): δ 12.80 (s, 1H), 8.82 (s, 1H), 8.00 (d, J=8.0 Hz, 1H), 7.88 (d, J=7.6 Hz, 1H), 7.62 (t, J=7.6 Hz, 1H), 7.49-7.43 (m, 3H), 7.37 (s, 1H), 7.32 (t, J=8.0 Hz, 1H), 6.88 (dd, J$_1$=8.4 Hz, J$_2$=2.0 Hz, 1H), 3.80 (s, 3H). $^{13}$C NMR (100 MHz, DMSO-d$_6$): 168.67, 168.52, 159.99, 150.90, 140.75, 136.52, 135.04, 132.36, 130.81, 130.40, 130.12, 129.26, 126.43, 118.41, 113.80, 111.31, 104.71, 55.52. HRMS (ESI) calcd for C$_{18}$H$_{14}$N$_3$O$_3$S [M−H]$^-$ 352.0756, found 352.0754. Purity: 95.56% (t$_R$ 7.94 min).

(E)-2-((2-(4-(3-aminoformylphenyl)thiazol-2-yl)hydrazono)methyl)benzoic Acid (53)

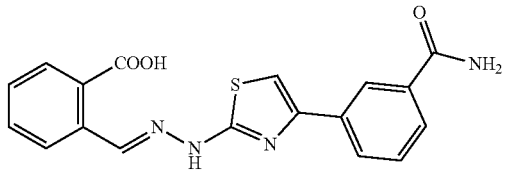 [SMILES: NC(=O)c1cccc(-c2csc(N/N=C/c3ccccc3C(=O)O)n2)c1]

Mp: 297.9-298.4° C. $^1$H NMR (400 MHz, DMSO-d$_6$): δ 12.20 (s, 1H), 8.83 (s, 1H), 8.39 (s, 1H), 8.05 (s, 1H), 8.00 (dd, J$_1$=7.2 Hz, J$_2$=3.2 Hz, 2H), 7.88 (d, J=7.6 Hz, 1H), 7.80 (d, J=7.6 Hz, 1H), 7.63 (t, J=7.6 Hz, 1H), 7.51-7.46 (m, 2H), 7.41 (s, 2H). $^{13}$C NMR (100 MHz, DMSO-d$_6$): 168.77, 168.67, 168.44, 150.57, 140.83, 135.19, 135.14, 135.02, 132.40, 130.83, 130.36, 129.31, 129.03, 128.62, 126.91, 126.46, 125.36, 105.00. HRMS (ESI) calcd for C$_{18}$H$_{15}$N$_4$O$_3$S [M+H]$^+$ 367.0865, found 367.0863. Purity: 97.89% (t$_R$ 7.832 min).

(E)-2-((2-(4-(p-tolyl)thiazol-2-yl)hydrazono)methyl)benzoic Acid (54)

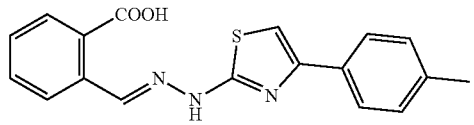 [SMILES: Cc1ccc(-c2csc(N/N=C/c3ccccc3C(=O)O)n2)cc1]

Mp: 225.5-226.1° C. $^1$H NMR (400 MHz, DMSO-d$_6$): δ 12.80 (s, 1H), 8.83 (s, 1H), 8.00 (d, J=7.2 Hz, 1H), 7.88 (d, J=7.6 Hz, 1H), 7.75 (d, J=8.0 Hz, 2H), 7.62 (t, J=7.6 Hz, 1H), 7.47 (t, J=7.6 Hz, 1H), 7.25 (s, 1H), 7.21 (t, J=8.0 Hz, 2H), 2.32 (s, 3H). $^{13}$C NMR (100 MHz, DMSO-d$_6$): 168.73, 168.55, 151.12, 140.69, 137.26, 135.04, 132.50, 132.29, 130.80, 130.56, 129.63, 129.22, 126.39, 125.96, 103.37, 21.27. HRMS (ESI) calcd for C$_{18}$H$_{14}$N$_3$O$_2$S [M−H]$^-$ 336.0807, found 336.0808. Purity: 96.31% (t$_R$ 13.17 min).

(E)-2-((2-(4-(2,5-dichlorophenyl)thiazol-2-yl)hydrazono)methyl)benzoic Acid (55)

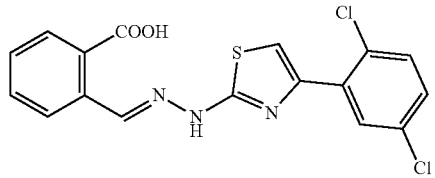 [SMILES: O=C(O)c1ccccc1/C=N/Nc1nc(-c2cc(Cl)ccc2Cl)cs1]

Mp: 205.0-206.0° C. $^1$H NMR (400 MHz, DMSO-d$_6$): δ 12.20 (s, 1H), 8.84 (s, 1H), 7.99 (d, J=7.2 Hz, 1H), 7.95 (d, J=6.4 Hz, 1H), 7.88 (d, J=8.0 Hz, 1H), 7.62 (t, J=7.2 Hz, 1H), 7.57 (d, J=8.4 Hz, 1H), 7.52 (s, 1H), 7.47 (t, J=7.6 Hz, 1H), 7.41 (dd, J$_1$=8.8 Hz, J$_2$=2.8 Hz, 1H). $^{13}$C NMR (100

MHz, DMSO-d$_6$): 168.67, 167.90, 146.07, 141.15, 135.02, 134.92, 132.65, 132.33, 132.28, 130.82, 130.74, 130.62, 129.74, 129.35, 129.03, 126.46, 110.57. HRMS (ESI) calcd for C$_{17}$H$_{10}$N$_3$O$_2$SCl$_2$ [M–H]$^-$ 389.9871, found 389.9871. Purity: 97.66% ($t_R$ 9.88 min).

(E)-2-((2-(4-(naphthalen-2-yl)thiazol-2-yl)hydra-zono)methyl)benzoic Acid (56)

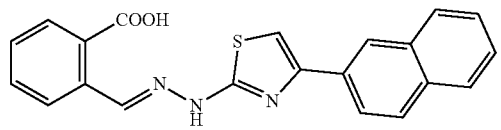 [SMILES: O=C(O)c1ccccc1/C=N/Nc1nc(-c2ccc3ccccc3c2)cs1]

Mp: 238.1–239.4° C. $^1$H NMR (400 MHz, DMSO-d$_6$): δ 12.80 (s, 1H), 8.87 (s, 1H), 8.40 (s, 1H), 8.04-8.01 (m, 2H), 7.96-7.89 (m, 4H), 7.64 (t, J=7.6 Hz, 1H), 7.54-7.46 (m, 4H). $^{13}$C NMR (100 MHz, DMSO-d$_6$): 168.75, 168.68, 151.02, 140.83, 135.07, 133.65, 132.92, 132.58, 132.40, 130.85, 130.39, 129.29, 128.63, 128.57, 128.05, 126.90, 126.47, 124.57, 124.43, 105.15. HRMS (ESI) calcd for C$_{21}$H$_{16}$N$_3$O$_2$S [M+H]$^+$ 374.0963, found 374.0959. Purity: 96.39% ($t_R$ 19.11 min).

(E)-2-((2-(4-(biphenyl-4-yl)thiazol-2-yl)hydrazono)methyl)benzoic Acid (57)

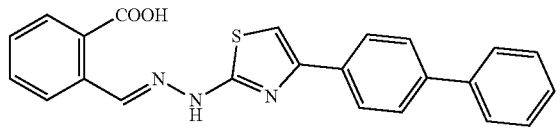 [SMILES: O=C(O)c1ccccc1/C=N/Nc1nc(-c2ccc(-c3ccccc3)cc2)cs1]

Mp: 227.1–228.1° C. $^1$H NMR (400 MHz, DMSO-d$_6$): δ 12.35 (s, 1H), 8.83 (s, 1H), 8.01 (d, J=6.0 Hz, 1H), 7.96 (d, J=6.8 Hz, 2H), 7.88 (d, J=6.0 Hz, 1H), 7.74-7.71 (m, 4H), 7.64 (t, J=6.4 Hz, 1H), 7.48 (t, J=6.0 Hz, 3H), 7.42 (s, 1H), 7.38 (t, J=6.0 Hz, 1H). $^{13}$C NMR (100 MHz, DMSO-d$_6$): 169.31, 169.31, 151.40, 141.42, 140.82, 140.22, 135.75, 134.93, 133.11, 131.52, 130.98, 130.12, 129.97, 128.62, 127.99, 127.63, 127.26, 127.14, 105.26. HRMS (ESI) calcd for C$_{23}$H$_{18}$N$_3$O$_2$S [M+H]$^+$ 400.1120, found 400.1114. Purity: 97.60% ($t_R$ 9.16 min).

(E)-2-((2-(4-(2-chlorophenyl)thiazol-2-yl)hydra-zono)methyl)-6-fluorobenzoic Acid (58)

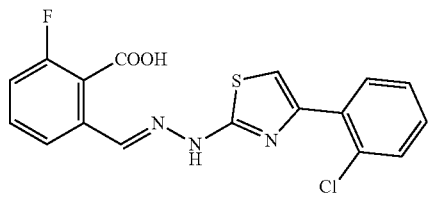 [SMILES: O=C(O)c1c(F)cccc1/C=N/Nc1nc(-c2ccccc2Cl)cs1]

Mp: 211.2–211.7° C. $^1$H NMR (400 MHz, DMSO-d$_6$): δ 12.40 (s, 1H), 8.18 (s, 1H), 7.86 (dd, J$_1$=7.6 Hz, J$_2$=1.6 Hz, 1H), 7.69 (d, J=8.0 Hz, 1H), 7.55-7.50 (m, 2H), 7.41 (t, J=7.6 Hz, 1H), 7.37 (s, 1H), 7.35 (t, J=7.6 Hz, 1H), 7.29 (t, J=8.8 Hz, 1H). $^{13}$C NMR (100 MHz, DMSO-d$_6$): 167.56, 166.14, 160.51, 158.06, 147.64, 138.21, 138.17, 133.94, 133.89, 133.68, 131.54, 131.25, 130.83, 129.53, 127.72, 122.04, 116.51, 116.29, 109.58. HRMS (ESI) calcd for C$_{17}$H$_{10}$N$_3$O$_2$SClF [M–H]$^-$ 374.0166, found 374.0164. Purity: 97.09% ($t_R$ 12.05 min).

(E)-2-((2-(4-(2-chlorophenyl)thiazol-2-yl)hydra-zono)methyl)-3-amino fluorobenzoic Acid (59)

Mp 220.9–221.6° C. $^1$H NMR (400 MHz, DMSO-d$_6$): δ 12.8 (s, 1H), 11.1 (s, 1H), 7.93 (s, 1H), 7.89 (d, J=7.2 Hz, 1H), 7.62 (d, J=7.6 Hz, 1H), 7.52-7.43 (m, 3H), 7.12 (d, J=7.2 Hz, 1H), 7.08 (d, J=8.4 Hz, 1H), 6.77 (s, 2H). $^{13}$C NMR (100 MHz, DMSO-d$_6$): δ 165.84, 155.22, 154.28, 147.07, 146.30, 133.99, 132.71, 131.65, 131.51, 131.09, 130.33, 129.73, 128.14, 121.28, 114.49, 113.14, 111.55. Purity: 97.06% ($t_R$ 19.58 min).

Example 2 (Activity Evaluation)

Activity Test for Inhibition of Viral Replication at Cellular Level

Determination of IC50 (half inhibitory concentration) of a drug: MDCK cells or Vero cells or RD cells were plated into 96-well plates, and grown to 90% or higher after 12 hours of culture. The drug was diluted in 2× gradient ($1 \times 10^{-1}$ to $1 \times 10^{-10}$). The culture of single-layer MDCK cells was aspirated, the cells were washed once with PBS, 50 μl of the corresponding drug dilution was added to each well, and 50 μl of virus solution (100 times TCID50) was added to each well, quadruplicate for each dilution. After incubated at 37° C., 5% CO$_2$ for 3-5 days, the production of CPE (cytopathic effect) was observed, the number of positive wells in the quadruplicate wells that can protect the cells from producing CPE (cytopathic effect) and the number of negative wells that can not protect the cells from producing CPE were recorded to find out the dilution factor of the drug which can inhibit half of the cells from producing cytopathic effect, and the IC50 of the drug was calculated according to Reed and Muench formula.

Determination of TC50 (half toxicity concentration) of a drug: MDCK cells or Vero cells or RD cells were plated into 96-well plates, and grown to 90% or higher after 12 hours of culture. The drug was diluted in 2× gradient ($1 \times 10^{-1}$ to $1 \times 10^{-10}$). The culture of single-layer MDCK cells was aspirated, the cells were washed once with PBS, and 100 μl of the corresponding drug dilution was added to each well, quadruplicate for each dilution. After incubated at 37° C., 5% CO$_2$ for 3-5 days, the cell death caused by drug toxicity was observed. The number of positive wells with cell death in the quadruplicate wells and the number of negative wells without cell death were recorded to find out the dilution factor of the drug causing half of cells death. The TC50 of the drug was calculated according to Reed and Muench formula.

Figure 2:
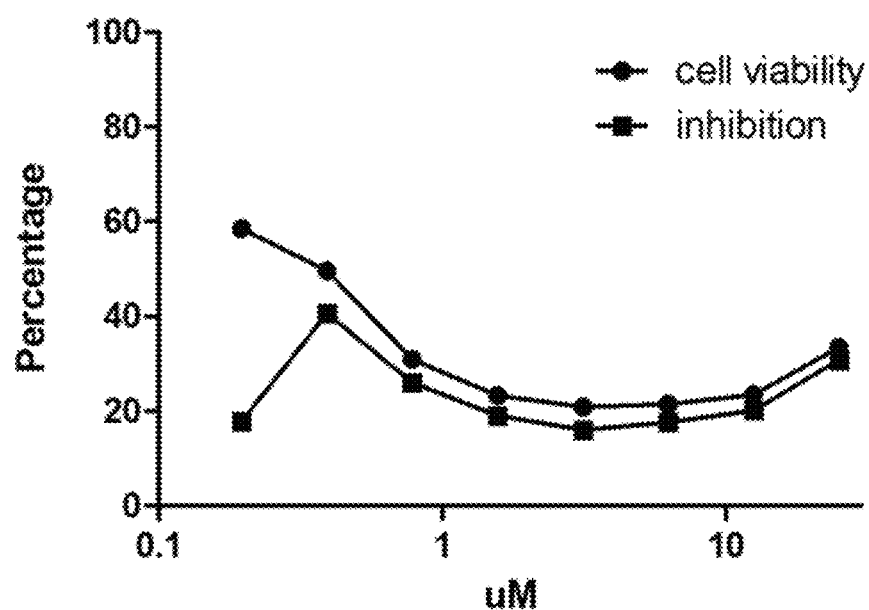
FIG. 2 shows inhibitory effects and cell survival curve of Compound 10 on human hand-foot-and-mouth virus EV71.
Figure 3:
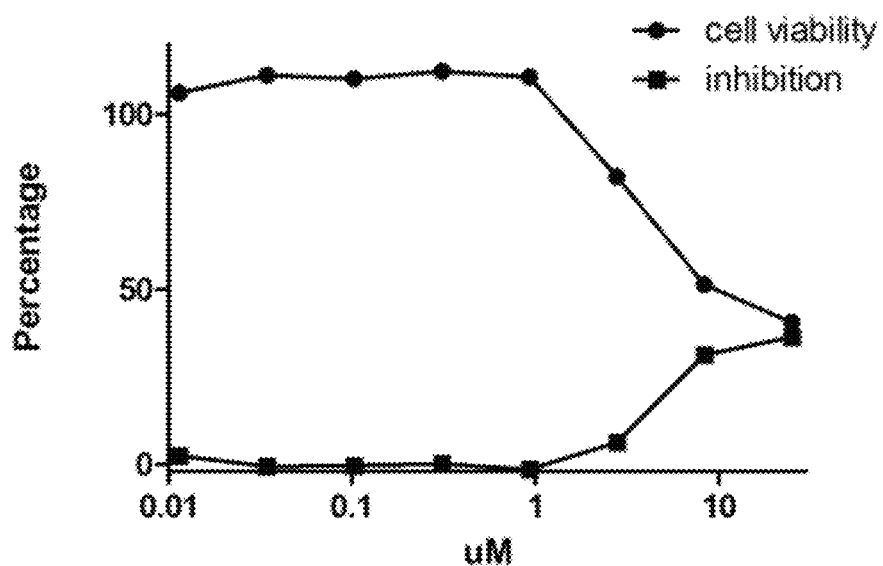
FIG. 3 shows inhibitory effects and cell survival curve of Compound 16 on human respiratory syncytial virus RSV.

The present inventors tested inhibitory effects of the compound of the present invention on cytopathic effects (CPE) caused by viral infection on mammalian cells. The results show that:

Compound 16 shows TC50 of >50 uM on MDCK host cell of influenza virus, and the inhibitory effect on influenza virus is about 2 uM (FIG. 1);

Compound 10 shows a certain inhibitory effects on human hand-foot-mouth virus EV71 (FIG. 2);

Compound 16 has a certain inhibitory effects on human respiratory syncytial virus RSV (FIG. 3).

Half-inhibitory concentration IC50 and half toxic concentration TC50 of the compound of the present invention against H3N2 (influenza virus) in host cell MDCK.

| Compound No. | IC50 (uM) | TC50 (uM) | SI (TC50/IC50) |
|---|---|---|---|
| 1 | 0.12 | 15 | 125 |
| 2 | 1.50 | 23 | 15 |
| 3 | 25 | 52 | 2.08 |
| 4 | 112 | 35 | 0.31 |
| 5 | 243 | 89 | 0.37 |
| 6 | 554 | 97 | 0.18 |
| 7 | 248 | 124 | 0.5 |
| 8 | 0.21 | 49 | 233 |
| 8-1 | 0.25 | 114 | 456 |
| 9 | 0.19 | 26 | 137 |
| 9-1 | 0.27 | 89 | 330 |
| 10 | 0.10 | 32 | 320 |
| 10-1 | 0.31 | 97 | 313 |
| 11 | 86 | 234 | 2.72 |
| 12 | 0.35 | 51 | 146 |
| 12-1 | 0.52 | 128 | 246 |
| 13 | 114 | 373 | 3.27 |
| 14 | 550 | 91 | 0.16 |
| 15 | 351 | 88 | |
| 16 | 0.20 | >50 | >250 |
| 17 | 1.5 | 94 | 62.6 |
| 18 | 45 | 148 | 3.3 |
| 19 | 0.9 | 43 | 47.8 |
| 20 | 5.2 | 57 | 11 |
| 21 | 2.5 | 49 | 19.6 |
| 22 | 248 | 415 | 1.6 |
| 23-1 | 0.26 | 124 | 477 |
| 24 | 152 | | |
| 25 | 742 | | |
| 52 | 147 | | |
| 53 | 216 | | |
| 54 | 326 | | |
| 55 | 12 | 547 | 45.6 |
| 56 | 549 | | |
| 57 | 4428 | | |
| 58 | 365 | | |
| 59 | 1542 | | |

Half-inhibitory concentration IC50 and half toxic concentration TC50 of the compound against H1N1 (influenza virus) in host cell MDCK.

| Compound No. | IC50 (uM) | TC50 (uM) | SI (TC50/IC50) |
|---|---|---|---|
| 1 | 0.42 | 35 | 83 |
| 2 | 3.69 | 29 | 8 |
| 3 | 12.3 | 86 | 7 |
| 4 | 2.6 | 23 | 8.8 |
| 5 | 52 | 68 | 1.3 |
| 6 | 124 | 451 | 2 |
| 7 | 221 | 355 | 1.6 |
| 8 | 0.63 | 31 | 49 |
| 8-1 | 0.89 | 123 | 138 |
| 9 | 0.27 | 65 | 240 |
| 9-1 | 0.36 | 235 | 653 |
| 10 | 0.21 | 49 | 233 |
| 10-1 | 0.39 | 240 | 615 |
| 11 | 5.1 | 241 | 47 |
| 12 | 0.79 | 61 | 77 |
| 12-1 | 0.91 | 329 | 362 |
| 13 | 65 | 87 | 1.3 |
| 14 | 41 | 88 | 2.1 |
| 15 | 124 | 412 | 3.3 |
| 16 | 0.5 | >50 | >100 |
| 17 | 8.1 | 561 | 7 |
| 18 | 10.2 | 124 | 12 |
| 19 | 0.56 | 26 | 46 |
| 20 | 2.5 | 57 | 22.8 |
| 21 | 5.4 | 41 | 7.6 |
| 22 | 55 | 148 | 2.7 |
| 23 | 0.39 | 87 | 223 |
| 23-1 | 0.67 | 201 | 300 |
| 24 | 325 | | |
| 25 | 485 | | |
| 52 | 1240 | | |
| 53 | 781 | | |
| 54 | 112 | | |
| 55 | 8.2 | 412 | 50 |
| 56 | 2310 | | |
| 57 | 1291 | | |
| 58 | 5.6 | 254 | 45 |
| 59 | 3324 | | |

Half-inhibitory concentration IC50 and half toxic concentration TC50 of the compound against H7N9 (influenza virus) in host cell MDCK.

| Compound No. | IC50 (uM) | TC50 (uM) | SI (TC50/IC50) |
|---|---|---|---|
| 1 | 2.32 | 26 | 11 |
| 2 | 5.73 | 45 | 8 |
| 8 | 0.59 | 39 | 66 |
| 8-1 | 0.86 | 96 | 117 |
| 9 | 0.53 | 44 | 83 |
| 9-1 | 0.67 | 219 | 327 |
| 10 | 0.28 | 45 | 161 |
| 10-1 | 0.49 | 253 | 516 |
| 11 | 14 | 54 | |
| 12 | 1.09 | 59 | 54 |
| 12-1 | 2.30 | 248 | 108 |
| 16 | 1.2 | >50 | >41.7 |
| 23 | 0.35 | 54 | |
| 23-1 | 0.67 | 102 | 152 |
| 55 | 6.9 | 624 | |

Half-inhibitory concentration IC50 and half toxic concentration TC50 of the compound against RSV (human respiratory syncytial virus) in host cell Vero (African green monkey kidney cell).

| Compound No. | IC50 (uM) | TC50 (uM) | SI (TC50/IC50) |
|---|---|---|---|
| 1 | 4.34 | 31 | 150 |
| 2 | 7.69 | 29 | 4 |
| 8 | 5.63 | 31 | 5.5 |
| 8-1 | 8.89 | 123 | 14 |
| 9 | 2.27 | 35 | 15 |
| 9-1 | 3.36 | 135 | 40 |
| 10 | 5.21 | 19 | 3.6 |
| 10-1 | 7.39 | 50 | 6.8 |
| 12 | 1.79 | 21 | 11.7 |
| 12-1 | 6.91 | 39 | 5.6 |

| Compound No. | IC50 (uM) | TC50 (uM) | SI (TC50/IC50) |
|---|---|---|---|
| 16 | 5.00 | 20 | 4 |
| 23-1 | 5.67 | 101 | 19 |
| 55 | 8.2 | 154 | 19 |

Half-inhibitory concentration IC50 and half toxic concentration TC50 of the compound against EV71 (hand-foot-and-mouth virus) in host cell RD (Human malignant embryonal rhabdomyoma cell).

| Compound No. | IC50 (uM) | TC50 (uM) | SI (TC50/IC50) |
|---|---|---|---|
| 1 | 0.14 | 1 | 7.1 |
| 2 | 0.23 | 1 | 4.3 |
| 8 | 0.09 | 1 | 11 |
| 8-1 | 0.19 | 2 | 10.5 |
| 9 | 0.12 | 1 | 8.3 |
| 9-1 | 0.33 | 3 | 9 |
| 10 | 0.05 | 0.5 | 10 |
| 10-1 | 0.18 | 1 | 5.6 |
| 12 | 0.25 | 1 | 4 |
| 12-1 | 0.39 | 2 | 5 |
| 16 | 0.30 | 1 | 3.3 |
| 23-1 | 0.37 | 2 | 5.4 |
| 55 | 0.51 | 3.1 | 6 |

Half-inhibitory concentration IC50 and half toxic concentration TC50 of the compound against Dengue Virus 2 (type 2 dengue virus) in host cell Vero (African green monkey kidney cell).

| Compound No. | IC50 (uM) | TC50 (uM) | SI (TC50/IC50) |
|---|---|---|---|
| 1 | 0.11 | 16 | 145 |
| 2 | 0.35 | 24 | 68.6 |
| 8 | 0.09 | 19 | 211 |
| 8-1 | 0.20 | 65 | 325 |
| 9 | 0.17 | 18 | 106 |
| 9-1 | 0.31 | 39 | 125.8 |
| 10 | 0.05 | 23 | 460 |
| 10-1 | 0.15 | 45 | 300 |
| 12 | 0.26 | 17 | 65 |
| 12-1 | 0.39 | 23 | 59 |
| 16 | 0.12 | 20 | 167 |
| 23-1 | 0.39 | 78 | 200 |
| 55 | 0.63 | 69 | 110 |

Half-inhibitory concentration IC50 and half toxic concentration TC50 of the compound against Zika Virus in host cell Vero (African green monkey kidney cell).

| Compound No. | IC50 (uM) | TC50 (uM) | SI (TC50/IC50) |
|---|---|---|---|
| 1 | 0.10 | 13 | 130 |
| 2 | 0.45 | 24 | 53 |
| 8 | 0.12 | 19 | 158 |
| 8-1 | 0.25 | 66 | 264 |
| 9 | 0.15 | 15 | 100 |
| 9-1 | 0.33 | 42 | 127 |
| 10 | 0.06 | 21 | 350 |
| 10-1 | 0.17 | 89 | 523 |
| 12 | 0.23 | 13 | 56.5 |
| 12-1 | 0.30 | 33 | 110 |
| 16 | 0.15 | 20 | 133 |
| 23-1 | 0.29 | 76 | 262 |
| 55 | 0.33 | 68 | 206 |

Half-inhibitory concentration IC50 and half toxic concentration TC50 of the compound against JEV (Japanese encephalitis virus) in host cell Vero (African green monkey kidney cell).

| Compound No. | IC50 (uM) | TC50 (uM) | SI (TC50/IC50) |
|---|---|---|---|
| 1 | 0.15 | 12 | 80 |
| 2 | 0.35 | 16 | 45.7 |
| 8 | 0.10 | 17 | 170 |
| 8-1 | 0.23 | 36 | 156 |
| 9 | 0.15 | 11 | 73.3 |
| 9-1 | 0.32 | 32 | 100 |
| 10 | 0.06 | 13 | 216 |
| 10-1 | 0.16 | 49 | 306 |
| 12 | 0.13 | 13 | 100 |
| 12-1 | 0.31 | 43 | 138.7 |
| 16 | 0.20 | 20 | 100 |
| 23-1 | 0.29 | 36 | 124 |

Antiviral Activity Test of Infection in Mice In Vivo

Figure 4:
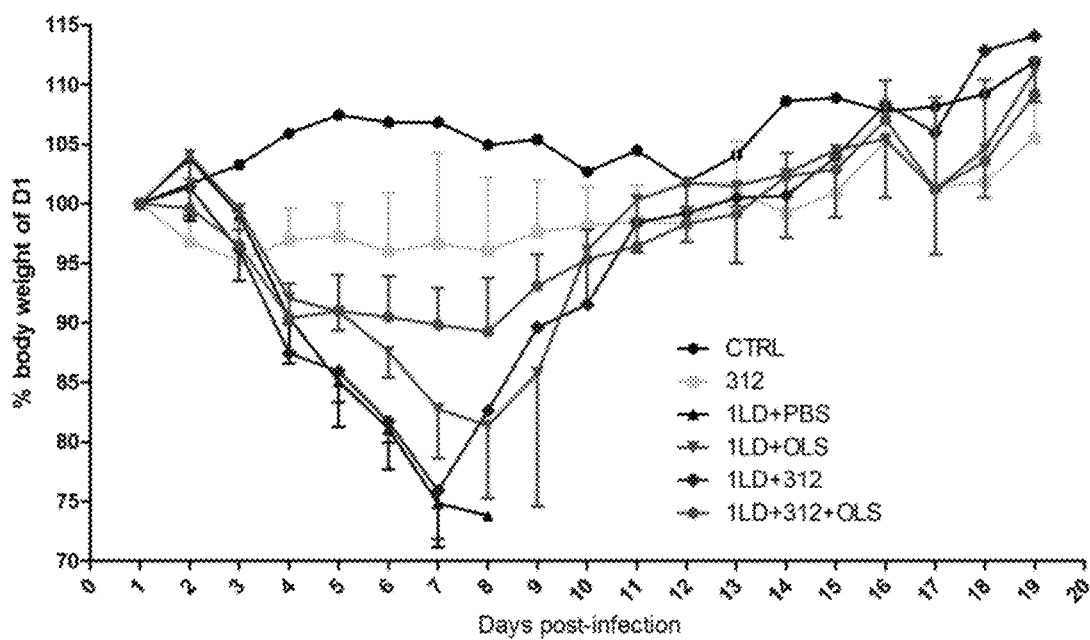
FIG. 4 shows curves of changes in body weight of mice after infection with a lethal dose of H7N9. CTRL: intraperitoneal injection of PBS, no infection with virus; 312 (Compound 16), intraperitoneal injection of 312, no infection with virus; 1LD+PBS: intraperitoneal injection of PBS, infection with virus; 1LD+OLS: intraperitoneal injection of Oseltamivir, infection with virus; 1LD+312: intraperitoneal injection of 312, infection with virus; 1LD+312+OLS: intraperitoneal injection of 312 and Oseltamivir, infection with virus. The drug was injected once a day for the first 5 days from the first day of infection.
Figure 5:
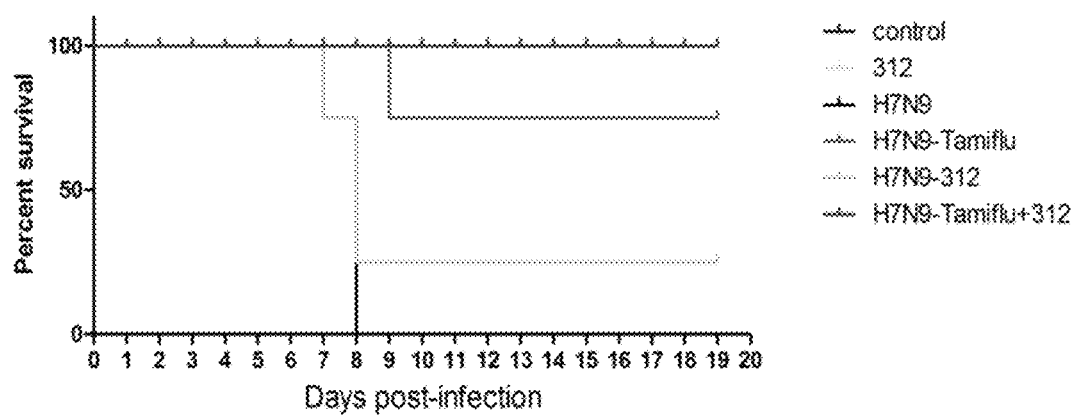
FIG. 5 shows the survival rate of drug-treated mice severely infected by H7N9, where 312 is Compound 16.

In a challenge experiment in mouse, mice were infected with a lethal dose of H7N9 avian influenza virus (1MLD50) through nasal administration. Compound 16 (10 mg/kg) can produce therapeutic effects similar to the positive drug Oseltamivir (OLS, 20 mg/kg), which exhibits as a recovery in the body weight of infected mice. Compound 16 can produce better effected if used in combination with Oseltamivir (FIG. 4). In terms of survival, the combination of Compound 16 and Oseltamivir can increase the survival rate of H7N9 heavily infected mice by 25% compared with Oseltamivir alone (FIG. 5).

Discussion:

Through in vitro cell experiments and in vivo challenge experiments of mouse, the compounds of the present invention produce good effects against acute infectious viruses such as influenza virus, hand-foot-to-mouth virus and dengue virus, and if used in combination with existing antiviral drugs, for example, Oseltamivir, can increase the survival rate of H7N9 heavily infected mice by 25%. The compounds of the present invention possesses a prospect of being developed into a broad spectrum antiviral drug.

All documents mentioned in the present application are hereby incorporated by reference in their entireties as if each document is separately cited as a reference. In addition, it is to be understood that various modifications and changes may be made by a skilled person in the art, after reading the above teachings of the present invention, and the equivalent forms also fall within the scope defined by the claims appended hereto.

The invention claimed is:

1. A method for treating a viral infection, comprising administering a compound represented by the formula:

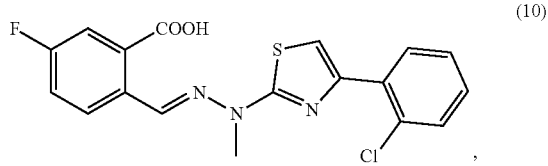 [SMILES: CN(/N=C/c1ccc(F)cc1C(=O)O)c1nc(-c2ccccc2Cl)cs1]
(10)

or a pharmaceutically acceptable salt thereof to a subject in need thereof.

2. A pharmaceutical composition comprising a compound of claim 1 or a pharmaceutically acceptable salt thereof in combination with other antiviral drugs, and a pharmaceutically acceptable carrier or excipient.

3. A method for treating viral infections, comprising administering a pharmaceutical composition of claim 2 to a subject in need of treatment of viral infections.

4. The method of claim 1, wherein the virus is an RNA virus selected from the group consisting of influenza virus, respiratory syncytial virus, hand-foot-and-mouth virus, dengue virus, Zika virus, and Japanese encephalitis virus.

5. The method of claim 4, wherein the hand-foot-and-mouth virus is EV71 virus, and the dengue virus is type 2 dengue virus.

6. A method for treating a viral infection, comprising administering a compound represented by the formula:

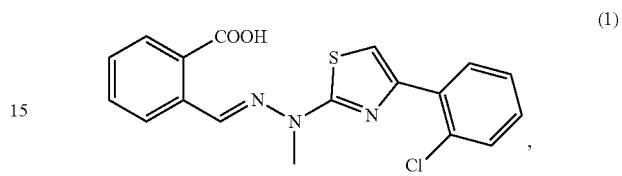
(1)

or a pharmaceutically acceptable salt thereof to a subject in need thereof, wherein the viral infection is caused by a respiratory syncytial virus.

* * * * *